(12) United States Patent
Nash et al.

(10) Patent No.: US 11,076,599 B2
(45) Date of Patent: Aug. 3, 2021

(54) ANTIMICROBIAL COATING COMPRISING CHALCOGENIDE NANO-PARTICLES CAPPED BY CHITOSAN

(71) Applicants: Kelly L. Nash, San Antonio, TX (US); Grégory Guisbiers, San Antonio, TX (US); Humberto Herman Lara Villegas, San Antonio, TX (US)

(72) Inventors: Kelly L. Nash, San Antonio, TX (US); Grégory Guisbiers, San Antonio, TX (US); Humberto Herman Lara Villegas, San Antonio, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 0 days.

(21) Appl. No.: 16/499,137

(22) PCT Filed: Mar. 28, 2018

(86) PCT No.: PCT/US2018/024795
§ 371 (c)(1),
(2) Date: Sep. 27, 2019

(87) PCT Pub. No.: WO2018/183464
PCT Pub. Date: Oct. 4, 2018

(65) Prior Publication Data
US 2020/0253214 A1    Aug. 13, 2020

Related U.S. Application Data

(60) Provisional application No. 62/477,821, filed on Mar. 28, 2017.

(51) Int. Cl.
*A01N 59/02* (2006.01)
*A01N 25/10* (2006.01)

(52) U.S. Cl.
CPC ............. *A01N 59/02* (2013.01); *A01N 25/10* (2013.01)

(58) Field of Classification Search
CPC ........ A01N 59/02; A01N 25/10; Y02A 50/30; A61K 33/30; A61K 31/722
See application file for complete search history.

(56) References Cited

U.S. PATENT DOCUMENTS

| 9,259,005 B2 | 2/2016 | Webster et al. |
| 2008/0147019 A1 | 6/2008 | Song et al. |
| (Continued) | | |

FOREIGN PATENT DOCUMENTS

| CN | 102560598 | 7/2012 |
| JP | 2004/155681 | 6/2004 |
| (Continued) | | |

OTHER PUBLICATIONS

Chhabria et al., Selenium Nanoparticles and their Applications, Encyclopedia or Nanoscience and Nanotechnology, American Scientific Publishers, (Year: 2016).*

(Continued)

*Primary Examiner* — Carlos A Azpuru
(74) *Attorney, Agent, or Firm* — Norton Rose Fulbright US LLP

(57) ABSTRACT

Disclosed herein are methods of making pure chalcogenide (e.g., selenium, tellurium, or selenium/tellurium) nanoparticles by irradiating chalcogenide pellets by nano-second laser ablation using chitosan as a capping agent to form chitosan chalcogenide nanoparticles (CS-CgNPs). CS-CgNPs and methods of using such particles are also disclosed herein, such as antimicrobials and antimicrobial coatings effective against biofilms.

8 Claims, 21 Drawing Sheets

(56) References Cited

U.S. PATENT DOCUMENTS

2012/0207846 A1  8/2012  Gao et al.
2016/0257694 A1  9/2016  Pi et al.

FOREIGN PATENT DOCUMENTS

JP   2007/145876   6/2007
JP   2007/518400   7/2012

OTHER PUBLICATIONS

Chhabria et al, "Selenium Nanoparticles and Their Applications",Encyclopedia of Nanoscience and Nanotechnology, pp. 1-32. (Year: 2016).*
Chatterjee, et al., "Biofilms on Indwelling Urologic Devices: Microbes and Antimicrobial Management Prospect," *Annals of Medical and Health Sciences Research*, 4; 100-104, 2014.
Cheung, et al., "Chitosan: An Update on Potential Biomedical and Pharmaceutical Applications," *Marine Drugs*, 13(8); 5156-5186, 2015.
Chhabria & Desai, "Selenium Nanoparticles and Their Applications," Encyclopedia of Nanoscience and Nanotechnology, Chapter: Selenium Nanoparticles and Their Applications, Publisher : American Scientific Publishers, Editors: Dr. H. Nalwa, pp. 1-32, Sep. 5, 2016.
Chou, "Drug Combination Studies and Their Synergy Quantification Using the Chou-Talalay Method," *Cancer Research*, 70(2); 440-446, 2010.
Dai, et al., "Chitosan Preparations for Wounds and Burns: Antimicrobial and Wound-Healing Effects," *Expert Review of Anti-Infective Therapy*, 9(7); 857-879, 2011.
Delaloye & Calandra, Invasive Candidiasis as a Cause of Sepsis in the Critically Ill Patient, *Virulence*, 5(1); 161-169, 2014.
Di Veroli, et al., "An Automated Fitting Procedure and Software for Dose-Response Curves with Multiphasic Features," *Science Reports*, 5; 14701, 2015.
Foucquier & Guedj, "Analysis of Drug Combinations: Current Methodological Landscape," Pharmacology Research & Perspectives, 3(3): e00149, 2015.
Guisbiers, et al., "Anti-Bacterial Selenium Nanoparticles Produced by UV/VIS/NIR Pulsed Nanosecond Laser Ablation in Liquids," *Laser Physics Letters*, 12(1); 016003, 2014.
Guisbiers, et al., "Synthesis of Tunable Tellurium Nanoparticles," *Semiconductor Science & Technology*, 32; 04LT01, 2017.
Harriott & Noverr, "Importance of Candida-Bacterial Polymicrobial Biofilms in Disease," *Trends in Microbiology*, 19(11); 557-563, 2011.
International Search Report and Written Opinion Issued in Corresponding PCT Application No. PCT/US2018/24795, dated Jul. 12, 2018.
Kieliszek et al., "Effects of Selenium on Morphological Changes in Candida Utilis ATCC 9950 Yeast Cells," *Biological Trace Element Research*, 169(2); 387-393, 2016.
Kieliszek, et al., "Accumulation and Metabolism of Selenium by Yeast Cells," *Applied Microbiology and Biotechnology*, 99(13); 5373-5382, 2015.
Kuwajima, et al., "Automated Transmission-Mode Scanning Electron Microscopy (tSEM) for Large Volume Analysis at Nanoscale Resolution," *PLoS One*, 8: e59573, 2013.
Lara, et al., "Effect of Silver Nanoparticles on Candida Albicans Biofils: An Ultrastructural Study," *Journal of Nanobiotechnology*, 13: 91, 2015.
Mathé & Van Dijck, "Recent Insights Into Candida Albicans Biofilm Resistance Mechanisms," *Current Genetics*, 59(4); 251-264, 2013.
Mayer, et al., "Candida Albicans Pathogenicity Mechanisms," *Virulence*, 4(2): 119-128, 2013.
Peña, et al., "Effects of Chitosan on Candida Albicans: Conditions for Its Antifungal Activity," *Biomed Research International*, 2013; 527549, 2013.
Pierce & Lopez-Ribot, "Candidiasis Drug Discovery and Development: New Approaches Targeting Virulence for Discovering and Identifying New Drugs," *Expert Opinion on Drug Discovery*, 8; 1117-1126, 2013.
Pierce, et al., "A 96 Well Microtiter Plate-Based Method for Monitoring Formation and Antifungal Susceptibility Testing of Candida Albicans Biofilms," *Journal of Visual Experiments*, 44; 2287, 2010.
Pierce, et al., "A Simple and Reproducible 96-Well Plate-Based Method for the Formation of Fungal Biofilms and Its Application to Antifungal Susceptibility Testing," *Nature Protocols*, 3(9); 1494-1500, 2008.
Pierce, et al., "Antifungal Therapy with an Emphasis on Biofilms," *Current Opinion in Pharmacology*, 13(5); 726-730, 2013.
Pierce, et al., "High Content Phenotypic Screenings to Identify Inhibitors of Candida Albicans Biofilm Formation and Filamentation," *Pathogens and Disease*, 70(3); 423-431, 2014.
Ramage, et al., "Fungal Biofilm Resistance," *International Journal of Microbiology*, 2012; 528521, 2012.
Rao, et al., "Chitosan-Decorated Selenium Nanoparticles as Protein Carriers to Improve the In Vivo Half-Life of the Peptide Therapeutic BAY 55-9837 for Tyle 2 Diabetes Mellitus," *International Journal of Nanomedicine*, 9; 4819-4828, 2014.
Tinggi, "Selenium: Its Role as Antioxidant in Human Health," *Environmental Health and Preventative Medicine*, 13(2);102-108, 2008.
Tran, et al., "Low Cytotoxic Trace Element Selenium Nanoparticles and Their Differential Antimicrobial Properties Against S. Aureus and *E. Coli*," *Nanotechnology*, 27(4); 045101, 2016.
Yu, et al., "Positive Surface Charge Enhances Selective Cellular Uptake and Anticancer Efficacy of Selenium Nanoparticles," *Inorganic Chemistry*, 51(16); 8956-8963, 2012.

\* cited by examiner

Types of Foley Catheters

Robinson one-way catheter ("straight cath")

Robinson two-way catheter, silicon

Coude two-way catheter, latex

Robinson three-way catheter, latex

Textile Protection against Fungus and Bacteria

Just after Synthesis

Just after Washing

ANTIMICROBIAL COATING COMPRISING CHALCOGENIDE NANO-PARTICLES CAPPED BY CHITOSAN

CROSS-REFERENCE TO RELATED APPLICATION

This application is a national phase under 35 U.S.C. § 371 of International Application No. PCT/US2018/024795, filed Mar. 28, 2018, which claims the benefit of priority to U.S. Provisional Patent Application Ser. No. 62/477,821, filed Mar. 28, 2017, the entire contents of each of which are hereby incorporated by reference in their entirety.

BACKGROUND

A biofilm is a structure that contains one or more types of microorganisms that are gathered and/or adhered to a living or non-living surface. Beneficial and pathogenic microbes secrete extracellular polymeric substances which form a matrix around groups of individual cells. Naturally occurring biofilms have multiple genera within the matrix; they are polymicrobial. Pathogens have multiple forms such as aerobic, anaerobic, and persister cells in the biofilm. Single cell pathogens can join the biofilm, or leave the biofilm. Groups of pathogens in matrix can detach from the biofilm. Single-celled pathogens within a biofilm communicate by way of signal molecules, which is termed quorum sensing. These signals are both intra- and inter-specie. Biofilms are known to cause serious problems in human bodies, environments, and in medicine generally. In the human body, a biofilm can cause disease and infection. In the environment, biofilms can be a cause of slime, clogging, and malodor in drains, pipes, air vents, etc. In some cases, biofilm formed on the surface of equipment necessary for food processing results in food poisoning due to contamination of the food during or after processing. In medicine, biofilms formed on the surface of a catheter or on hospital devices may be the source of serious infections.

A number of methods and compositions are known to inhibit or remove biofilms. For example, a composition has been described for oral use incorporating sugar alcohol and/or amino acids to suppress adhesion, aggregation or the like of bacteria in the process of forming biofilm (JP Appl. 2007-145876). Other reports describe an oral biofilm inhibitor that includes a lactone derivative and/or a furan derivative that can effectively control oral bacteria and biofilm that cause oral diseases (JP Appl. 2004-155681). Still other reports describe a cell-free fermentation product derived from one or more types of fermentative bacteria selected from *Lactobacillus* species, *Lactococcus* species, and *Pediococcus* species that prevents biofilm formation, reduces existing biofilm, and decreases populations of bacteria (JP Appl. 2007-518400).

Despite the availability of antimicrobial compositions, there is a continuing need to develop additional drugs and treatments to overcome, inhibit, or prevent biofilm formation.

SUMMARY

One solution to the biofilm problem is to treat a biofilm or a target surface by applying or coating a target surface with chitosan stabilized chalcogenide nanoparticles. The chitosan stabilized chalcogenide nanoparticles treat, prevent, or inhibit biofilm formation. Described below are methods for synthesizing chitosan (CS) stabilized chalcogenide nanoparticles by irradiating chalcogenide (selenium, tellurium, or selenium/tellurium) pellets with chitosan using nano-second, pico-second, femto-second pulsed laser ablation. In some instances, the synthesis of chalcogenide nanoparticles is performed by irradiating chalcogenide pellets submersed in deionized (DI) water with CS by nano-second laser ablation at 1064 nm using CS as a capping agent forming chitosan stabilized chalcogenide nanoparticles (CS-CgNPs). In some instances, irradiation is achieved by using a pulsed nanosecond Nd-YAG laser with a wavelength in the UV spectrum of light (355 nm) or Visible spectrum of light (532 nm). As a non-limiting example these CS-CgNPs can be used in various applications to prevent, inhibit, or treat biofilm formation.

As described below, CS-CgNPs display potent activity against biofilm forming organisms, e.g., *Candida albicans*, at a non-cytotoxic range. CS-CgNPs have been tested against a pre-formed mature biofilm of *C. albicans*, showing a synergistic fungicidal effect. The combination of CgNPs and CS demonstrate a synergistic activity against *C. albicans* biofilms as measured by a well-established phenotypic assays (Pierce et al., *Nat. Protoc.* 2008, 3:1494-500; Pierce et al., *J. Vis. Exp.* 2010; Pierce and Lopez-Ribot, *Expert Opin. Drug Discov.* 2013, 8:1117-26) and by Compusyn software (Chou, *Cancer Res.* 2010, 70:440-6; Chang and Chou, *Acta Paediatr.* Taiwan 41:294-302).

CS-CgNPs (e.g., CS-SeNPs, CS-TeNPs, CS-SeTeNPs) can be used as antimicrobial coatings on materials such as glass, plastic, stainless steel, titanium, etc. Laser ablation enables the synthesis of chitosan-stabilized pure chalcogenide nanoparticles without contaminants produced by additives and these CS-CgNPs have demonstrated efficient dose-dependent activity against preformed biofilms of *C. albicans*. The results show a potent synergistic effect of the combination of CgNPs and CS on inhibition of a mature biofilm.

Certain embodiments are directed to methods for producing an antimicrobial coating on a surface, the method comprising: mixing chitosan capped chalcogenide (e.g., selenium, tellurium or selenium-tellurium alloy) nanoparticles (CS-CgNPs) with an application material to form a mixture; applying the mixture on the surface forming a surface having a chitosan capped chalcogenide nanoparticles on or in the surface that inhibit biofilm formation. The biofilm can comprise a bacteria, a fungi, or combinations thereof. In certain aspects the biofilm comprises *Staphylococcus aureus, Candida albicans, Pseudomonas aeruginosa, Streptococcus, E. coli* or combinations thereof. The chitosan capped chalcogenide nanoparticles can be present or distributed on the surface at a density of about 0.05, 0.15, 0.30 to 1.0 mg/m². In certain aspects the surface density is about 0.15 mg/m². In certain aspects a chalcogenide nanoparticle is a selenium, tellurium, or selenium/tellurium nanoparticle.

The CS-CgNPs can be present in the mixture in an amount from about 0.0001 wt. % to about 10 wt. %. In certain aspects the CS-CgNPs have an average diameter between 60 to 100 nanometers. The surface can be a medical device, a textile surface, a pipe or tube surface, a cooking surface, or the like.

Other embodiments are directed to an article having an antimicrobial surface, the article comprising at least one surface having a plurality of chitosan capped selenium nanoparticles distributed across the surface. In certain aspects the CS-CgNPs are present at a density of ~0.15 mg/m². The CS-CgNPs can have an average diameter between about 10 nanometers and about 100 nanometers. In certain aspects the article can be a medical device, a textile, a pipe or tube, or other surface susceptible to biofilm formation.

Certain embodiments are directed to methods for inhibiting a biofilm, the method comprising: applying chitosan capped selenium nanoparticles (CS-SeNPs) at a concentration of 0.001 to 0.12 mg/ml (1 to 120 ppm) to a surface for inhibiting biofilm formation. Uncapped Se nanoparticles showed low toxicity below 128 ppm (Nanotechnology (2016) vol. 27, 045101).

Other embodiments include chitosan capped chalcogenide nanoparticle compositions comprising chitosan capped chalcogenide nanoparticles suspended in an application material. In certain aspects the application material is an ointment, paint, or an evaporable or removable carrier.

"Medical devices" are herein defined as disposable or permanent catheters, (e.g., central venous catheters, dialysis catheters, long-term tunneled central venous catheters, short-term central venous catheters, peripherally inserted central catheters, peripheral venous catheters, pulmonary artery Swan-Ganz catheters, urinary catheters, and peritoneal catheters), long-term urinary devices, tissue bonding urinary devices, vascular grafts, vascular catheter ports, wound drain tubes, ventricular catheters, hydrocephalus shunts, heart valves, heart assist devices (e.g., left ventricular assist devices), pacemaker capsules, incontinence devices, penile implants, small or temporary joint replacements, urinary dilator, cannulas, elastomers, hydrogels, surgical instruments, dental instruments, tubings, such as intravenous tubes, breathing tubes, dental water lines, dental drain tubes, and feeding tubes, fabrics, paper, indicator strips (e.g., paper indicator strips or plastic indicator strips), adhesives (e.g., hydrogel adhesives, hot-melt adhesives, or solvent-based adhesives), bandages, orthopedic implants, bone scaffolds, bone implants, dental fillings, dental implants, and any other device used in the medical field. "Medical devices" also include any device which may be inserted or implanted into a human being or other animal, or placed at the insertion or implantation site such as the skin near the insertion or implantation site, and which include at least one surface which is susceptible to colonization by a biofilm forming microorganism.

Other surfaces for which it may be desired or necessary to prevent biofilm include surfaces of equipment in operating rooms, emergency rooms, hospital rooms, clinics, and bathrooms. In certain aspects, one or more composition described herein is integrated into an adhesive, such as tape, thereby providing an adhesive which may prevent growth or proliferation of biofilm at least one surface of the adhesive.

An article or medical device being treated or coated may be formed of any suitable metallic materials or non-metallic materials known to persons skilled in the art. Examples of metallic materials include, but are not limited to, tivanium, titanium, and stainless steel, and derivatives or combinations thereof. Examples of non-metallic materials include, but are. not limited to, thermoplastic or polymeric materials such as rubber, plastic, polyesters, polyethylene, polyurethane, silicone, Gortex (polytetrafluoroethylene), Dacron (polyethylene tetraphthalate), Teflon) (polytetrafluoroethylene), latex, elastomers and Dacront) sealed with gelatin, collagen or albumin, and derivatives or combinations thereof. The articles or medical devices being treated or coated have at least one surface for applying the CS-SeNPs composition. The CS-SeNPs composition can be applied to all surfaces or a portion of the medical device.

The term "effective concentration" or "effective amount" is defined as a sufficient amount of the CS-SeNPs to substantially prevent the growth or proliferation of biofilm or organisms that form such a biofilm, particularly on a surface of a medical device. The amount may vary based upon known factors such as pharmaceutical characteristics; the type of medical device; the degree of biofilm or microorganism contamination; and the use and length of use. It is within the ability of a person of ordinary skill in the art to relatively easily determine an effective concentration for CS-SeNPs.

The terms "inhibiting," "reducing," or "prevention," or any variation of these terms, when used in the claims and/or the specification includes any measurable decrease or complete inhibition of biofilm formation.

The term "chalcogenide" or "chalcogenides" refers to materials that comprise selenium, tellurium, or selenium-tellurium alloy.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, devices, compositions, and kits of the invention can be used to achieve methods of the invention.

The use of the word "a" or "an" when used in conjunction with the term "comprising" in the claims and/or the specification may mean "one," but it is also consistent with the meaning of 'one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE FIGURES

The following drawings form part of the present specification and are included to further demonstrate certain aspects of the present invention. The invention may be better understood by reference to one or more of these drawings in combination with the detailed description of the specification embodiments presented herein.

DESCRIPTION

Figure 1A:
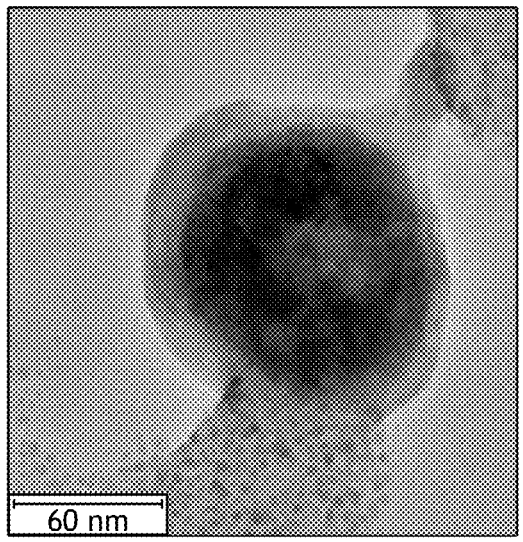
FIG. 1a-1d. High resolution transmission electron microscope (HRTEM) images of a large and small CS-SeNPs (a and c, respectively). Electron diffraction pattern of large and small CS-SeNPs (b and d, respectively) indicate that both are crystalline in nature.

One of the microorganisms that is found in biofilms is *Candida albicans*. *Candida albicans* is a major opportunistic fungal pathogen capable of causing a broad spectrum of human diseases. Candidiasis is now the fourth most frequent nosocomial blood stream infection (BSI) in the US causing severe fungal sepsis (Delaloye and Calandra, *Virulence* 2014, 5:161-9). One of the most important virulence factors that contributes to the pathogenesis of candidiasis is its ability to form biofilms, communities of cells attached to a substrate and enveloped by a protective extracellular matrix (Harriott and Noverr, Trends Microbiol. 2011, 19:557-63). Indwelling prosthetic materials and most catheters represent ideal surfaces for the development of *Candida* biofilms. Consequently, *Candida* is the most frequently isolated fungal pathogen in catheter-related bloodstream infection (CRBSI) resulting in high morbidity and mortality rates in hospitalized patients (Gahlot et al., *Int. J. Crit. Illn. Inj. Sci.* 2014, 4:162-7). *Candida* biofilms are enclosed by an exopolymeric substance or EPS matrix which protects the pathogen from adverse exposure to environmental conditions (Mahe and Van Dijck, *Curr. Genet.* 2013, 59:251-64), host's immune defense, and the action of systemic antifungal agents. Moreover, detached yeast from the biofilm are the source of sepsis by spreading the BSI (Chatterjee et al., *Ann. Med. Health Sci. Res.* 2014, 4:100-4). Morphogenetic conversions between yeast and hyphae have a key role in biofilm formation and represent an important virulence factor for disease pathogenesis (Mayer et al., *Virulence* 2013, 4:119-28). The main characteristic of biofilms is their high level of antifungal drug resistance, as cells within the biofilms can endure up to 1,000-fold greater concentrations of antimycotics compared to planktonic cells (Taff et al., *Future Microbiol.* 2013, 8:1325-37). Due to significant morbidity and mortality rates associated with biofilm-associated candidiasis, there is an urgency to develop novel compounds to overcome biofilm drug resistance. *Staphylococcus aureus* is one of the most dangerous bacteria, responsible for a countless number of human infections worldwide. Since the emergence of the methicillin-resistant *Staphylococcus aureus* (MRSA), multiresistant strains of MRSA have become a serious infectious problem. MRSA's biofilm formation has been recognized as the most important mechanism associated with prolonged and recurrent infections of implanted medical devices.

Selenium (Se) is a naturally occurring element essential as a nutrient for human, animal, and plant organisms. It belongs to the oxygen family (group 16 in the periodic table: oxygen, sulfur, selenium, tellurium, polonium) therefore it does not oxidize in air and is insoluble in water. Se is already present in our body as a trace element. Se has important health benefits due to its critical role of inhibiting the formation of free radicals, therefore prevents oxidative stress, a major source of age-related diseases, such as cancer or cardiovascular diseases (Tinggi, Environ. *Health Prev. Med.* 13 2008, 13:102-8). However in high quantities Se becomes toxic, showing a narrow margin between beneficial and toxic effects (Rao et al., *Int. J. Nanomedicine* 2014, 9:4819-28). Yeast of the genus *Candida* have the ability to accumulate extensive quantities of trace elements such as Se integrated into organic compounds (Kieliszek et al., *Appl. Microbiol. Biotechnol.* 2015, 99:5373-82). The mechanisms of accumulation and transformation of Se into the cell wall architecture of *C. albicans* remains elusive (Kieliszek et al., *Appl. Microbiol. Biotechnol.* 2015, 99:5373-82). Selenium enters the yeast by binding based on chemisorption with the formation of ionic bonds of Se ions by cell-wall polymers. The fungicidal effect of this essential trace element may be due to the absorption of selenium in the yeast cell and mixing with cell proteins in which Se displaces sulfur (due to chemical analogy of both elements), for sulfur-containing amino acids cysteine (Cys) and methionine (Met)(Kieliszek et al., *Appl. Microbiol. Biotechnol.* 2015, 99:5373-82). Yeast absorb selenium into the cytosol, using transporters such as sulfate permeases Sul1 and Sul2 where these oxyanions utilize both sulfate transporters to enter (Herreo and Wellinger, *Microb. Cell* 2015, 2:139-49) [14]. Se and Selenoproteins have a well-known beneficial antioxidant effect (Tinggi, Environ. *Health Prev. Med.* 2008, 13:102-8), but in excess generates reactive oxygen species (ROS), which in turn can induce oxidative stress with DNA strand breaks. This process can lead to changes in protein misfolding, stability, structure changes, and also to enzymes dysfunction. Toxic activity of inorganic selenium compounds in the yeasts involves reaction of selenites with thiol-containing compounds (Kieliszek et al., *Biol. Trace Elem. Res.* 169 (2016) 169:387-93).

Chitosan (CS) is a linear polysaccharide derivative of chitin, mostly extracted from fungi, arthropods such as crustaceans, and insects. CS is a biocompatible, natural, biodegradable, positively charged polymer with low cytotoxicity (Cheung et al., *Mar. Drugs* 2015, 13:5156-86). Microbicidal properties of CS as a polycationic natural polymer is well established and studies revealed the permeabilization of yeast cells as the main fungicidal effect (Peña et al., *Biomed Res. Int.* 2013, 527-49). The polycationic agents of the polymer interact with anionic components of the yeast cell wall reducing the negative surface charge of the yeast resulting from the strong attachment of the biopolymer permeabilizing the outer cell membrane as result (Peña et al., *Biomed Res. Int.* 2013, 527-49; Dai et al., *Expert Rev. Anti. Infect. Ther.* 2011, 9:857-79).

I. Chitosan Stabilized Nanoparticles

Selenium nanoparticles (SeNPs) were synthesized by irradiating selenium pellets, either with or without chitosan present, with a pulsed laser at a wavelength of 355 nm, 532 nm or 1064 nm aimed vertically from above into the selenium pellet containing solution. The laser pulses can be nano-second, pico-second or femto-second in duration. The selenium pellet(s) are irradiated for an appropriate time producing a red-orange or gray solution. The selenium nanoparticles produced in the presence of chitosan are washed to remove the excess chitosan. An acid wash can be performed using a 50/50 solution of acetic acid and DI water by adding to the sample and then centrifuging to produce a pellet. The pellet(s) can be suspended into PBS solution and concentration of the solution determined by atomic absorption spectrophotometer using a selenium or tellurium lamp and known concentration of ion standards.

As shown herein, using advanced electron microscopy (EM), CS-SeNPs permeabilize the outer cell membrane of *C. albicans* and changes the characteristic spherical structure of the *candida* cells. Not to be bound by theory, it is believed that the CS enables cell permeabilization and Se causes structural changes, such as protein misfolding. Further, it is believed that the synergistic effect of CS-SeNPs is at least in part attributed to an effective inhibition of the pre-formed mature biofilm.

The ability to synthesize contamination-free pure nanoparticles is desired, especially for medical applications. Herein is disclosed the synthesis of pure selenium nanoparticles by irradiating selenium pellets by pulsed laser ablation using chitosan as a capping agent (CS-SeNPs). These nanoparticles displayed a synergistic fungicidal effect on *C. albicans* biofilms. Using advanced electron microscopy techniques, it is shown herein that CS-SeNPs change the characteristic morphological structure of the *C. albicans* biofilm cells. In certain aspects the CS-SeNPs have a synergistic effect with an effective inhibition of the pre-formed mature biofilms. In a further aspect, the CS-SeNPs can be effectively used as an antimicrobial coating.

II. Formulation and Administration

Embodiments of the invention include applying or coating a CS—SeNP composition. Coating or applying includes the steps of dispersing CS-SeNPs on a surface or target, which inhibits or prevents the growth or proliferation of microorganisms on the surface or target. A CS—SeNP composition is formed by combining a CS—SeNP and a base or application material. At least one surface of a target is then contacted with the CS—SeNP composition under conditions wherein the CS—SeNP composition covers at least one surface of the target. "Contacting" or "applying" includes, but is not limited to, impregnating, compounding, mixing, integrating, coating, spraying, evaporation and dipping. In certain aspects the CS—SeNP composition is applied to a surface and allowed to dry.

In certain embodiments, the invention also provides compositions comprising CS-SeNPs with one or more of the following: an acceptable diluent; a carrier; a solubilizer; an emulsifier; and/or a preservative. Such compositions may contain an effective amount of CS-SeNPs. Thus, the use of CS-SeNPs that are provided herein in the preparation of a coating or treating composition is also included.

The CS-SeNPs may be formulated into therapeutic compositions in a variety of dosage forms such as, but not limited to, liquid solutions or suspensions, powders, paints, or coatings. An acceptable formulation of components for certain preparations are nontoxic to recipients or subjects that come in contact with the compositions at the dosages and concentrations employed. In addition to the CS-SeNPs provided, compositions may contain components for modifying, maintaining, or preserving, for example, the pH, viscosity, clarity, color, odor, sterility, stability, adsorption, or penetration of the composition. Suitable materials for formulating compositions include, but are not limited to, antimicrobials; antioxidants (such as ascorbic acid, sodium sulfite or sodium hydrogen-sulfite); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); suspending agents; surfactants or wetting agents (such as pluronics, PEG, sorbitan esters, polysorbates such as polysorbate 20, polysorbate 80, triton, tromethamine, lecithin, cholesterol, tyloxapal); delivery vehicles; diluents; and/or excipients. Formulation components are present in concentrations that are acceptable to the site of administration.

EXAMPLES

The following examples are included to demonstrate preferred embodiments of the invention. It should be appreciated by those of skill in the art that the techniques disclosed in the examples represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Synthesis of Selenium Nanoparticles in the Presence or Absence of Chitosan

Selenium nanoparticles (SeNPs) were synthesized for further testing. SeNPs produced according to one or more of the methods disclosed herein and those produced in the absence of chitosan were used for the comparison studies outlined below. The concentration of the solutions containing the SeNPs produced according to one or more of the methods disclosed herein was determined to be 25.5 ppm ±0.5.

Methodology—

Briefly, SeNPs were synthesized by placing 0.35 g of selenium pellets in a 1.7 mL microcentrifuge tube that contained 0.5 mL of DI water (to produce SeNPs) or 0.25% chitosan solution (to produce CS-SeNPs). A 3.6 nanosecond optical parametric oscillator (OPO) laser (NT342B, EKSPLA, Bozeman, Mont.) pumped by a 20 Hz Q-switched Nd: YAG powered at 20 mJ utilized at the $3^{rd}$ harmonic (355 nm) wavelength was aimed vertically from above into the open microcentrifuge tube where the beam focused on to the pellets. The target was irradiated for 15 minutes producing a red-orange color in the solution that was extracted for further analysis. The selenium nanoparticles produced in the 0.25% chitosan solution were washed to remove the excess chitosan from the sample. An acid wash was performed using a 50/50 solution of acetic acid and DI water by adding to the sample and then centrifuging to produce a pellet. The pellet was suspended into PBS solution. The concentration of the solutions was determined using an atomic absorption spectrophotometer (AA-6200, Shimadzu) using a selenium lamp (L2433-34NQ, Hamamatsu, Boston, Mass.).

Materials—

Selenium pellets (Se, <5 mm, <=99.999% Trace Metals, Sigma Aldrich), Tellurium Pellets (Te, <5 mm, <=99.99% Trace Metals, Sigma Aldrich), Selenium telluride ingot (SeTe<=99.999%, American Elements), chitosan (Chit, low, medium or high molecular weight), Sodium hydroxide (NaOH, ACS reagent, ≥97.0%, pellets), and acetic acid (ACS reagent, ≥99.7%) were purchased from Sigma Aldrich (St. Louis, Mo., USA). Molecular Biology Grade water (MT46000CM, Corning) was purchased from Fisher Scientific (Waltham, Mass.).

Example 2

Characterization of SeNPs

Figure 1B:
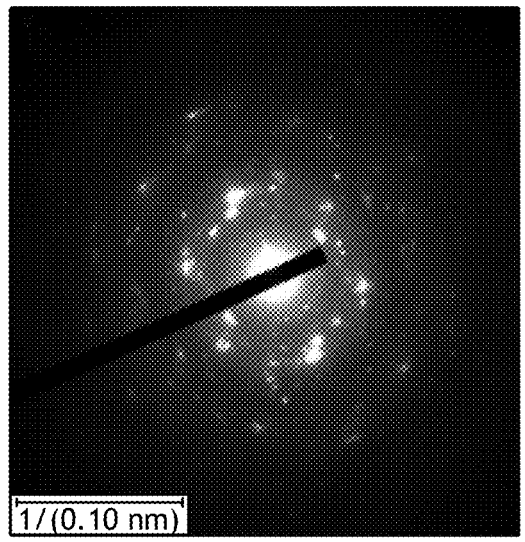
Figure 1C:
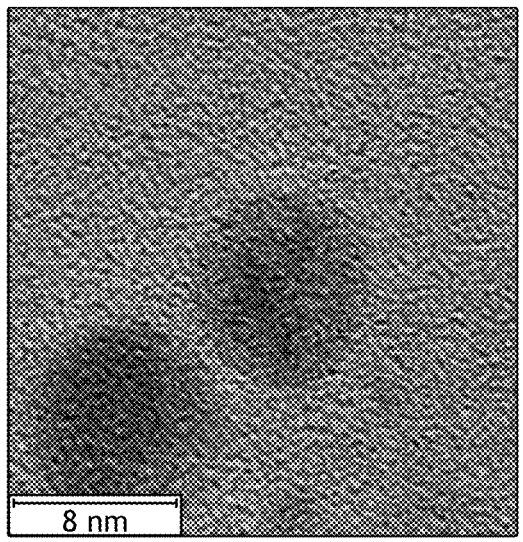
Figure 1D:
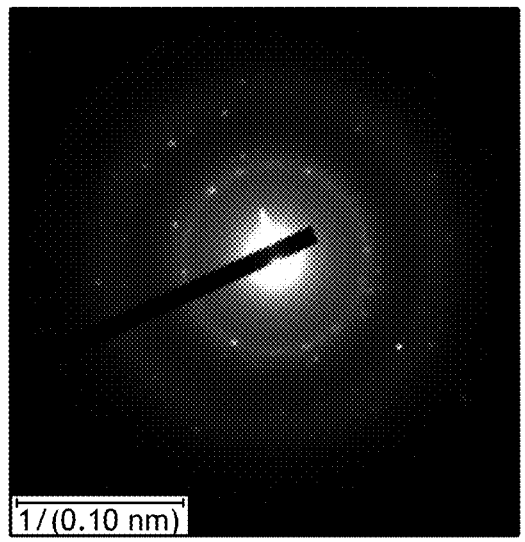
Figure 2A:
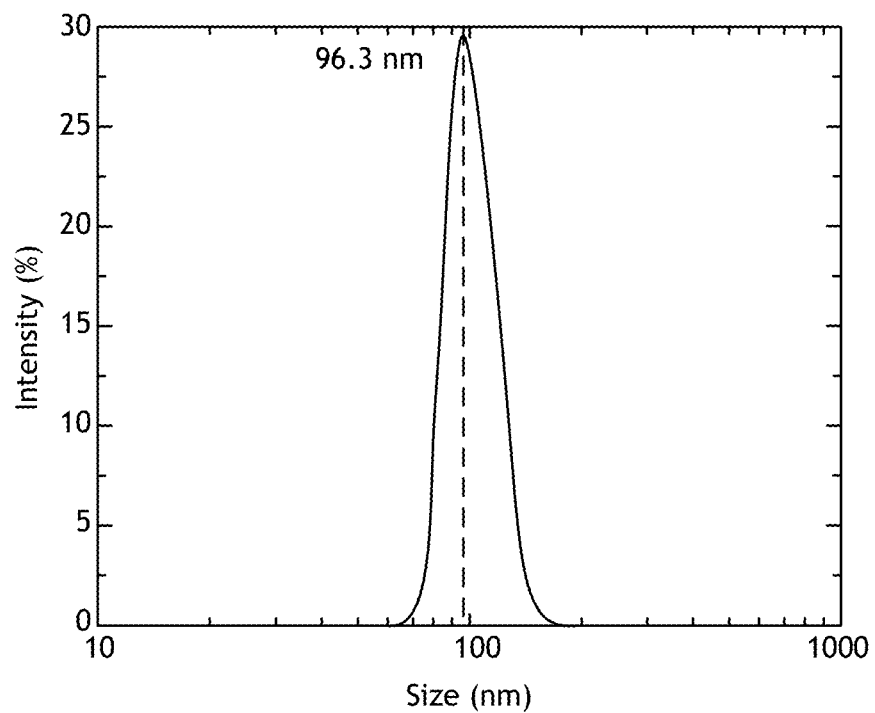
FIGS. 2a and 2b. Histogram of the size distribution of individual CS-SeNPs measured by dynamic light scattering (DLS) (a). The average size of nanoparticles is 96.3 nm. The Zeta potential showed a negative charge of −35.7 mV (b). If the zeta potential is higher than the absolute value ±30 mV then the solution is considered stable while below this value it is unstable and tends to flocculate.
Figure 2B:
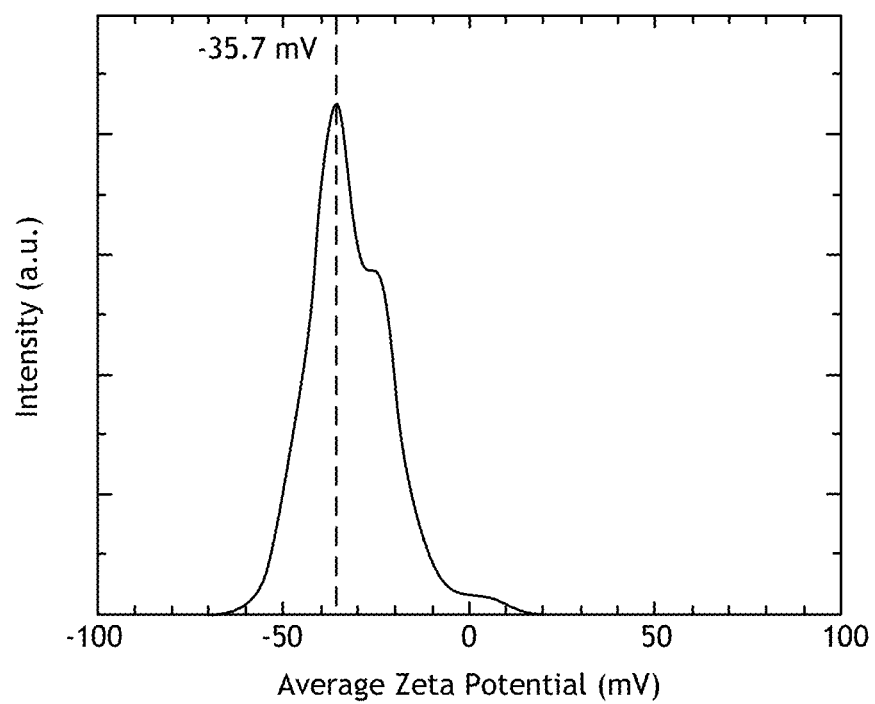

High resolution transmission electron microscope (HR-TEM) images of CS-SeNPs are shown in FIGS. 1a and 1c. The average size distribution of the CS-SeNPs were determined to be 93.3 nm (FIG. 2a). FIGS. 1b and 1d, show diffraction patterns of a small and large nanoparticle indicating that both are crystalline in nature. It was observed that the CS matrix surrounding the nanoparticle enhances the crystalline nature of the nanoparticle compared to the amorphous nature of selenium nanoparticles produced in DI water (Guisbiers et al., Laser Phys. Lett. 2015, 12:016003). Not to be bound by theory, this may be due to the amino acid groups in chitosan interacting with the surface of the selenium nanoparticle where the coordination behaviors of the nanoparticle increase the nanoparticle stability and enhance the crystallinity (Yu et al., Inorg. Chem. 51 2012, 51:8956-63). The stability of the CS-SeNPs was demonstrated by Zeta potential which had a negative charge of about −31.4 mV, which demonstrates that the binding effects of the chitosan to the nanoparticle enhances the stability of the nanoparticles (FIG. 2b). Dynamic light scattering (DLS) was performed on the CS-SeNPs indicating an average hydrodynamic radius of the nanoparticles of about 126.3 nm with a fairly large distribution. These results correlate with the observation of both large and small nanoparticles seen in TEM images. The larger sizes observed by the DLS can be attributed to larger particles shielding the smaller sizes from instrument measurement.

Methodology—

Briefly, hydrodynamic size and zeta potential (surface charge) of the selenium nanoparticles were characterized using the dynamic light scattering (DLS) system (Zetasizer Nano ZS, Malvern Instruments Inc. UK) at 25° C. The transmission electronic microscope (HRTEM, JOEL 2010F) atomic resolution microscope (ARM, JOEL ARM 200F) was used to acquire images of the selenium nanoparticles to determine the size and shape of the nanoparticles using the Cs probe at a voltage of 200 kv with a special resolution of 0.75 Å. The specially resolved elemental analysis was done by X-ray emission spectroscopy attachment to the HRTEM.

Example 3

Inhibition of Pre-Formed Biofilm

Biofilms formed by *C. albicans* and *Staphylococcus aureus*, MRSA, *Streptococcus, Candida albicans, Pseudomonas aeruginosa, E. coli* or combinations thereof are difficult to treat as sessile cells within the biofilm display intrinsic resistance to most conventional antifungals. Therefore, it is urgent to develop novel strategies that target biofilm related infections (Ramage et al., *Int. J. Microbiol.* 2012, 2012:528521). Herein, a well-established phenotypic assay (Pierce et al., *Pathog. Dis.* 2014, 70:423-31) is used to measure the inhibitory effect of selenium nanoparticles, chitosan and selenium nanoparticles capped with chitosan.

Figure 3A:
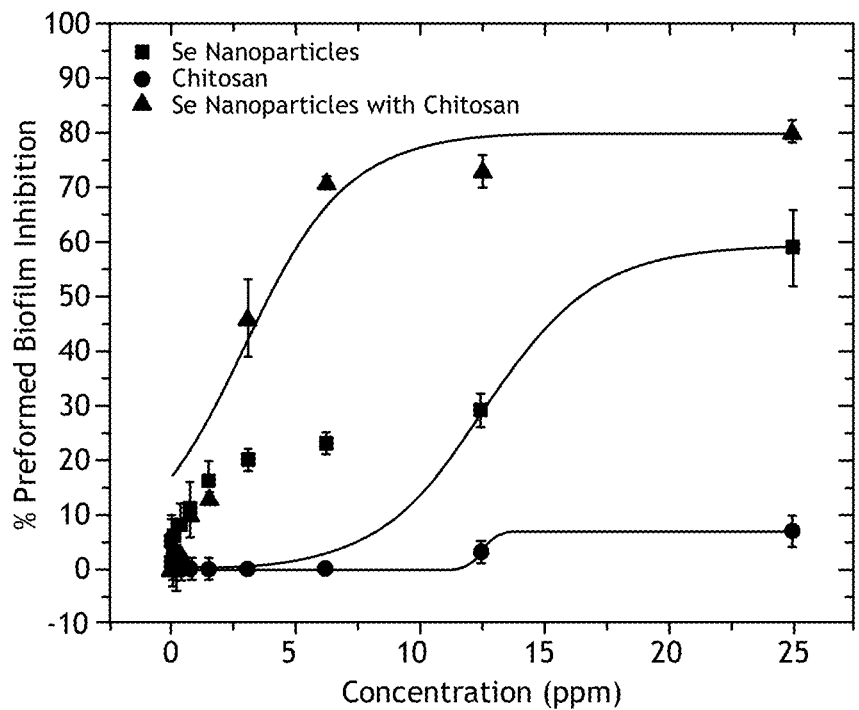
FIGS. 3a and 3b. (a) Dose-Response Curves for the activity of SeNPs, CS, and CS-SeNPs against *C. albicans* preformed biofilms. Different concentrations in two-fold serial dilutions were added to *C. albicans* mature biofilm. The $IC_{50}$ values were calculated as SeNPs 21.7 ppm and CS-SeNPs 3.52 ppm. (b) Cytotoxicity of CS-SeNPs in RPE-19 cells, the CC50 is 26.3 ppm. Cytotoxicity of CS-SeNPs was quantified by a Luciferase assay after 24 h of compound incubation. X-axis: concentration in ppm; Y-axis: % of cell cytotoxicity. Dose-response curves were plotted using Origin 9 curve fit. Each data point represents the mean±SEM of three independent experiments performed on different days.

Results indicated a dose-dependent inhibitory effect of SeNPs on the preformed *C. albicans* biofilms, with a calculated $IC_{50}$ of 21.7 ppm. Chitosan alone has also an inhibitory effect on the biofilm obtaining a 7% inhibition at 25 ppm. Selenium capped with Chitosan (Ch-SeNPs) had the most potent inhibition against preformed biofilms with an $IC_{50}$ of 3.5 ppm, which pointed to a strong synergistic effect when compared to both compounds alone (FIG. 3a). The $IC_{50}$ for TeNPS and SeTeNPs were calculated to be ~2.6 ppm and 1.5 ppm (Se)-2.0 ppm (Te), respectively.

Figure 3B:
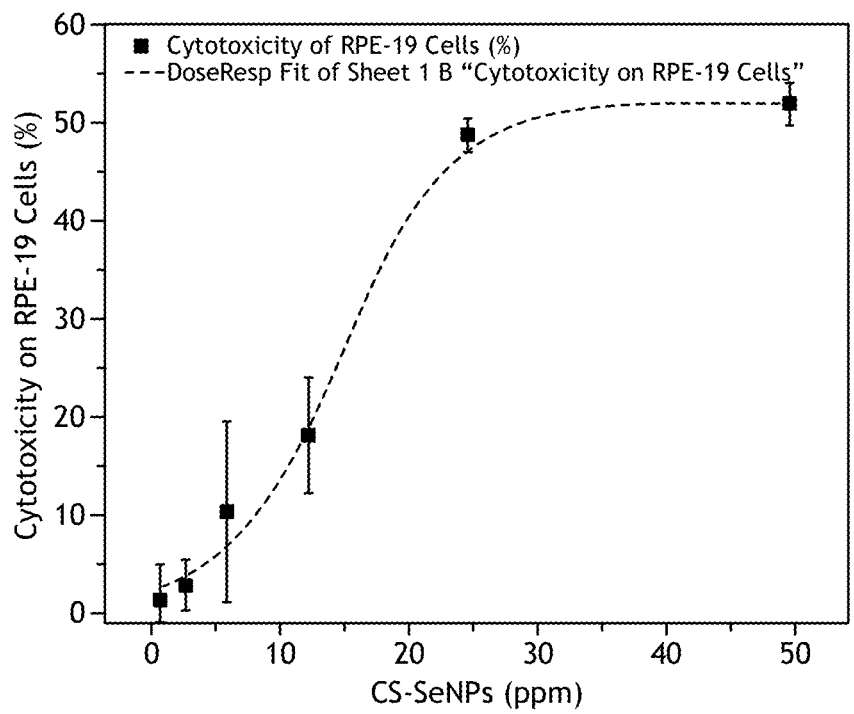
Figure 4:
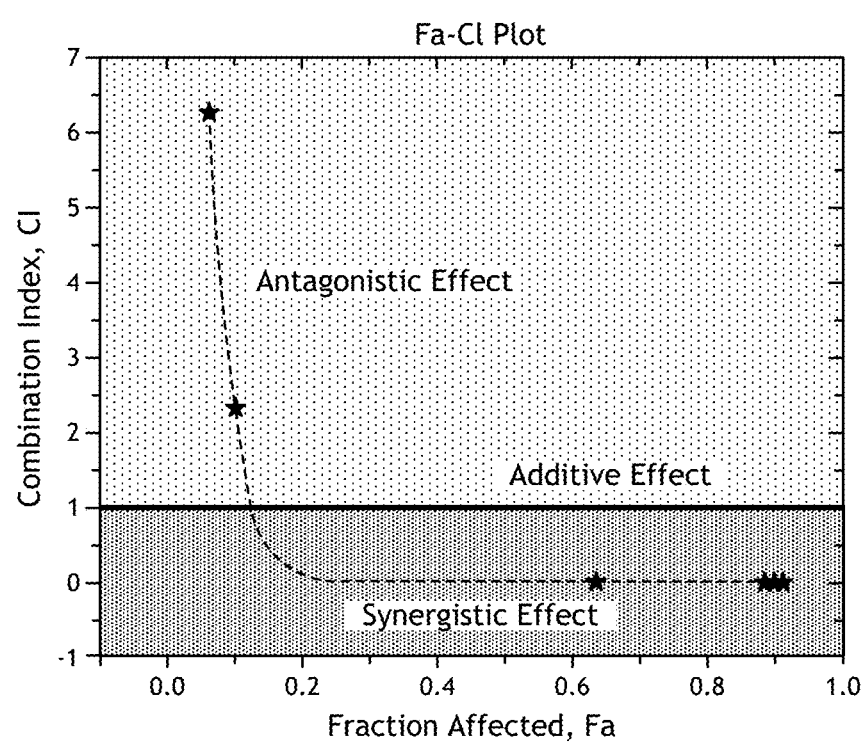
FIG. 4. The Combination index (CI) was determined using the Compusyn program algorithm to evaluate the interaction of CS with SeNPs (CS-SeNPs). The horizontal line marks CI=1. The CI offers definition for additive (CI=1), synergism (CI<1), and antagonism (CI>1) in drug combination. The data are the mean values from three independent experiments.

$IC_{50}$ calculations and dose-response fitting functions analyses were performed using Origin statistical/graphing software (Microcal, Northhampton, Mass.)(Di Veroli et al., Sci. Rep. 2015, 5:14701). CalcuSyn (Bijnsdorp et al., *Methods Mol. Biol.* 2011, 731:421-34) generated CI values according to the Chou-Talalay method (Chang and Chou, *Acta Paediatr. Taiwan* 41:294-302). The CS-SeNPs combination treatment was synergistic, with CI values <1 (FIG. 4). As determined by the cytotoxicity assay below (FIG. 3b), there was no significant difference in the viabilities of *Candida albicans* biofilm at the different drug concentrations tested, indicating that the synergistic action of CS and SeNPs was due to their fungicidal effect and not due to cytotoxicity.

Methodology—

Briefly, *C. albicans* wild type strain SC5314 was used in this study. Frozen cells from stocks stored at −80° C. were propagated in yeast-peptone-dextrose (YPD) agar plates, overnight at 30° C. Flasks containing 25 ml of YPD liquid media were inoculated with a loopful of the overnight *Candida* growth and incubated in an orbital shaker at 180 rpm at 30° C. and grown for 14-16 h. Biofilms were assessed using the 96-well microtiter plate-based method previously reported (Pierce et al., Nat. Protoc. 2008, 3:1494-500). Briefly, yeast cells collected from overnight cultures were washed in sterile PBS and resuspended in RPMI-1640 with biofilms formed on tissue culture-treated, 96-well polystyrene microtiter plates (Corning Incorporated) then incubated at 37° C. for 24 h. The biofilm formed and attached to the bottom of the 96-wells were washed twice with PBS to discharge any unbound yeasts cells. The biofilm inhibition was determined using semi-quantitative colorimetric technique based on the XTT reduction assay previously described (Pierce et al., *Curr. Opin. Pharmacol.* 2013, 13:726-30; Lara et al., *J. Nanobiotechnology* 2015, 13:91), with ODs determined spectrophotometrically utilizing a microtiter plate reader (Benchmark Microplate Reader). The OD of control biofilms formed in the absence of Ch-SeNPs was arbitrarily set at 100% and data was calculated as percent biofilm inhibition relative to the average of the control wells.

The activity against preformed biofilms of CS-SeNPs, CS-TeNPs, CS-SeTeNPs, SeNPs, and CS were assessed for their fungicidal activity against mature preformed biofilms, at different concentrations ranging from 0.024 to 25 ppm in serial two-fold dilutions using a methodology as previously described (Pierce et al., Nat. Protoc. 2008, 3:1494-500; Pierce et al., J. Vis. Exp. 2010; Lara et al., J. Nanobiotechnology 2015, 13:91). Briefly, to test the efficacy of CS-SeNPs, CS-TeNPs, CS-SeTeNPs, SeNPs and CS against pre-formed biofilms, 96 well microtiter wells were seeded with 100 μL of 1×106 cells/mL and incubated for 24 h. Then, 100 μL of different concentrations of nanoparticles were added to the mature biofilm. The well-plates were covered with parafilm to reduce evaporation and incubated for another 24 h. The plates were then carefully washed twice to discard non-adherent *Candida* cells and the fungal biofilm was quantified using an XTT reduction assay to test the efficacy of the nanoparticles preparations. All tests were performed in duplicate and were repeated at least three times in independent experiments. The IC50 was performed with the dose-response curves were analyzed using Origin 9 software (OriginLab Corporation, Northampton, Mass. USA)(Di Veroli et al., Sci. Rep. 2015, 5:14701).

To determine synergism, the Combination index (CI) theorem of Chou-Talalay analyses was used, a popular method to evaluate the synergistic interactions of the different combinations of drugs. Specifically, the method described by Chou et al. (*Cancer Res.* 2010, 70:440-6) using the computer software Calcusyn (Chang and Chou, *Acta Paediatr. Taiwan* 41:294-302; Bijnsdorp et al., *Methods Mol. Biol.* 2011, 731:421-34) was used. Briefly, to calculate synergism, additivity or antagonism, the (CI)-isobologram equation was used, where CI values around 1 demonstrate additive effects of the two drugs tested, CI<1 indicates a synergistic effect of the two drugs combined, and CI>1 indicates an antagonistic effect.

Graphs show values of the means from three separate experiments by dose-response fitting using Origin 9 software (OriginLab Corporation, Northampton, Mass. USA). For the synergism analysis we used the CalcuSyn Windows software for Combination Index (CI) theorem of Chou-Talalay (Chou, Cancer Res. 2010, 70:440-6; Chang and Chou, Acta Paediatr. Taiwan 41:294-302) following the developer's instructions using CalcuSyn software Version 2.0 (Biosoft UK).

Example 4

Cytotoxicity

The CS-SeNPs concentrations showing potent fungicidal effects against *C. albicans* mature biofilms are much lower than those at which they exhibit cytotoxicity. Cytotoxicity was demonstrated by a cytotoxicity assay using human ARPE cells, resulting in a $CC_{50}$ of 26.3 ppm (FIG. 3b).

Methodology—

Briefly, a stock solution of selenium nanoparticles was diluted to the desired concentrations ranging from 50 to 1 ppm in growth medium and subsequently added into 96-wells plates containing human retinal pigment epithelial cell line ARPE-19 ($5\times10^4$ cells/well). Microtiter plates were incubated at 37° C. in a 5% $CO_2$ air humidified atmosphere for 24 hours. Assessments of cell viability were carried out using a CellTiter-Glo® Luminescent Cell Viability Assay (Promega).

Example 5

Visualization of Effects on C. albicans Preformed Biofilms

Figure 5A:
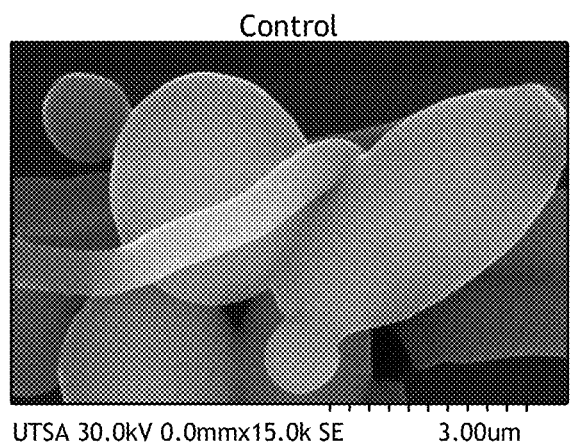
FIG. 5a-5d. Scanning Electron Microscopic ultrastructural visualization of (a) untreated *C. albicans* biofilms, (b) *C. albicans* SC5314 biofilms treated with chitosan at 0.025 mg/mL (25 ppm), (c) *C. albicans* treated with SeNPs at 0.0217 mg/mL (21.7 ppm), and (d) *C. albicans* treated with CS-SeNPs at 0.0035 mg/mL (3.5 ppm). All images are at 24 hours post-treatment. Biofilms grown in the absence of treatment demonstrated a dense network of yeast cells and hyphae, yeast cells show a characteristic ovoid morphology (a). In contrast, biofilms incubated with chitosan displayed enlarged and deformed yeast cells (b). (c) Yeasts treated with SeNPs (0.017 mg/mL) have changes in morphology (arrows). (d) Yeasts treated with CS-SeNPs 0.0035 mg/mL have changes in morphology and structure. Arrows show deformation on the yeast cells and the polycationic polymer adhering to the negatively charged outer cell surface.
Figure 5B:
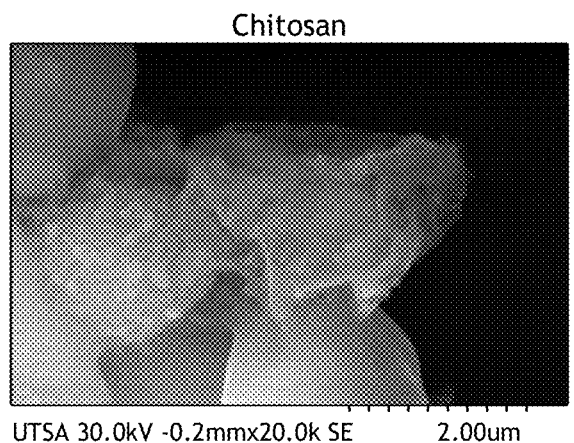
Figure 5C:
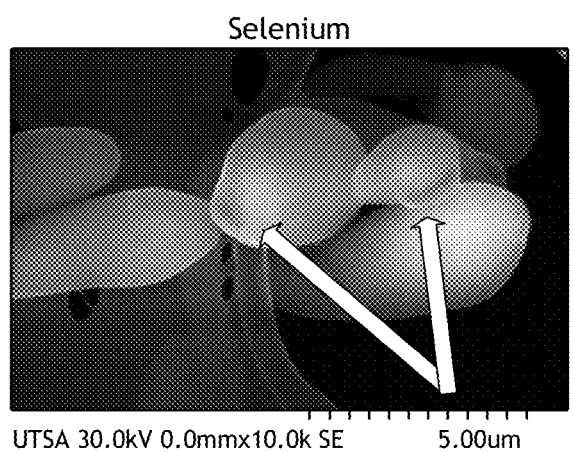
Figure 5D:
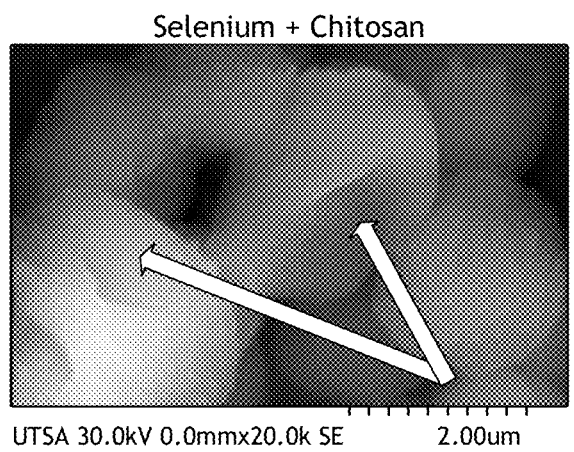
Figure 6A:
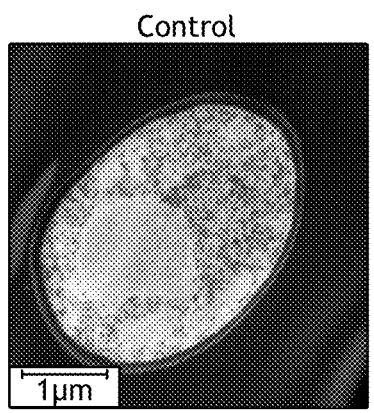
FIG. 6 (a) Untreated *Candida albicans* with characteristic ovoid morphology. (b) and (c) After 24 h treatment with CS-SeNPs at 3.5 ppm the cell loses the characteristic ovoid morphology as the cell distort, the outer cell disrupts and the CS-SeNPs enter the cell.
Figure 6B:
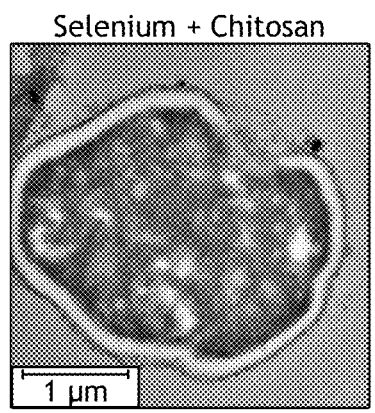
Figure 6C:
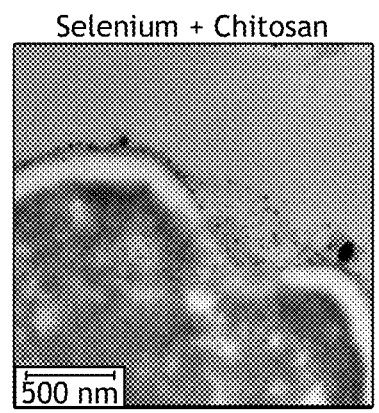

Scanning Electron Microscopy (SEM) was used to visualize three-dimensional surfaces of cells at high-resolution. SEM documented ultrastructural morphology of fungi as well as the interaction with nanoparticles, SEM also has an enhanced depth of field on the overall biofilm topology. Changes on ultrastructural morphologies of fungal cells within the biofilms were studied, both in the absence and in the presence of CS-SeNPs treatment. The ultrastructural changes were imaged under SEM with CS-SeNPs at 3.5 ppm treatment, documenting major changes on the structure of yeast. FIG. 5a shows untreated C. albicans SC5314 biofilms with dense network of yeast cells and hyphae, yeast show a characteristic ovoid morphology. FIG. 5b shows C. albicans biofilms treated with chitosan at 25 ppm displayed enlarged and deformed the yeast cells. C. albicans treated with SeNPs at 21.7 ppm (FIG. 5c) have changes in morphology (arrows). Yeasts treated with CS-SeNPs 3.5 ppm have changes in morphology and structure. Arrows show deformation on the yeast cells and the polycationic polymer adhere to the negatively charged outer cell surface (FIG. 5d). Bright-field (BF) STEM image shows CS-SeNPs nanoparticles entering the yeast (FIG. 6a). In the SEM-DF image of CS-SeNPs, CS is shown adhered to the outer cell membrane as a white substance that is wrapping the outer cell membrane of the yeast cell and the black dots are selenium nanoparticles (FIG. 6b).

Figure 7:
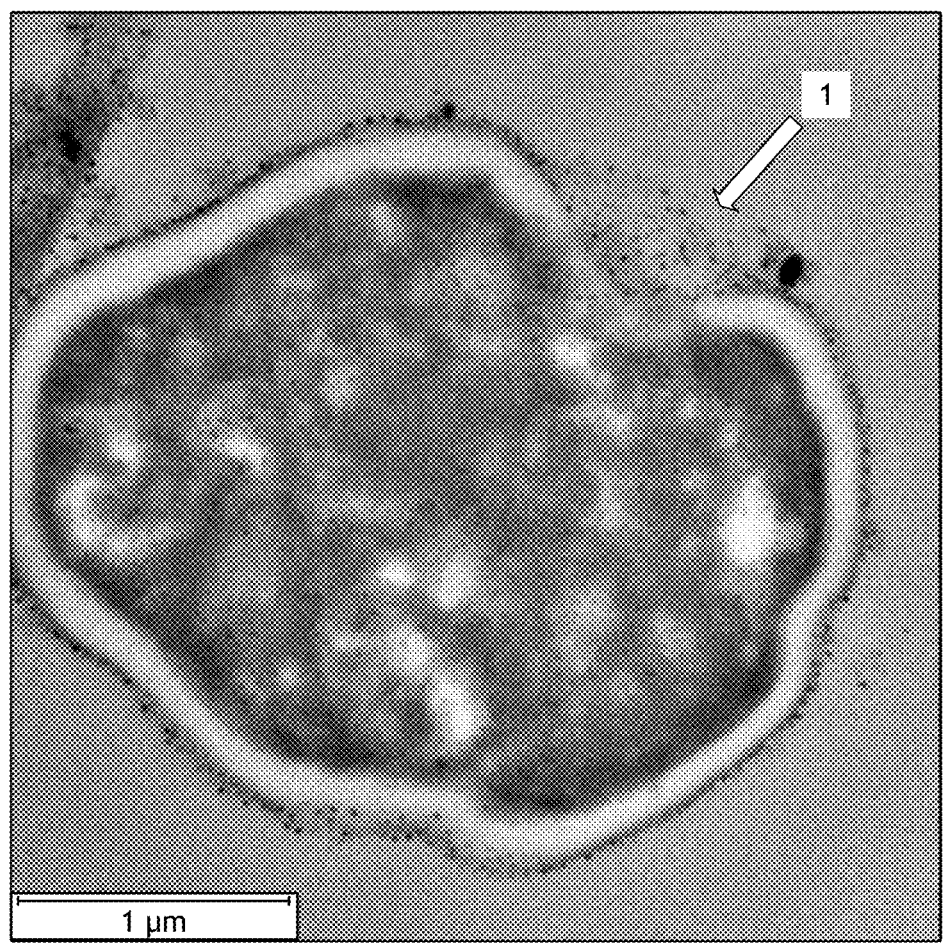
FIG. 7. TEM image of a *C. albicans* treated with CS-SeNPs. After 24 hours of treatment with CS-SeNPs at 0.0035 mg/mL, the cell loses the characteristic spherical morphology as the cell deforms, the outer cell disrupts allowing the nanoparticles enter the cell (white arrow).
Figure 8A:
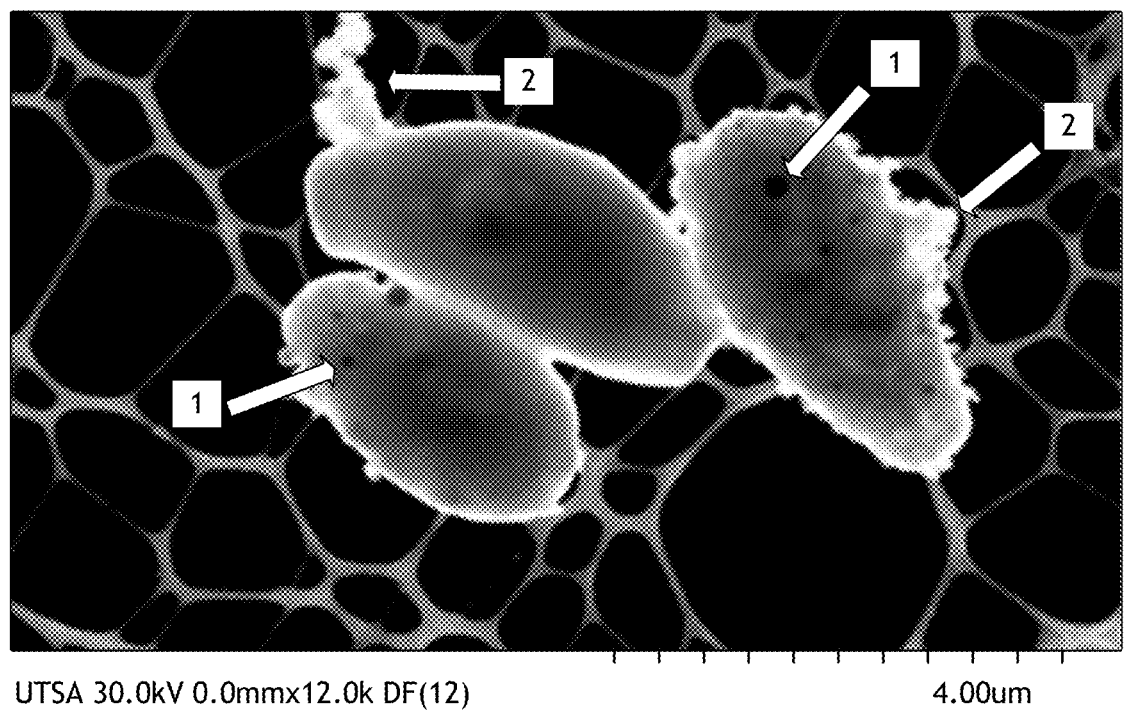
FIG. 8. Energy-dispersive X-ray spectroscopy (EDS) spectrum of SeNPs. Selenium EDS peaks are labeled. Strong signals from the atoms in the SeNPs observed in the spectrum confirm selenium metalloid nanoparticles on the yeast outer cell wall.
Figure 8B:
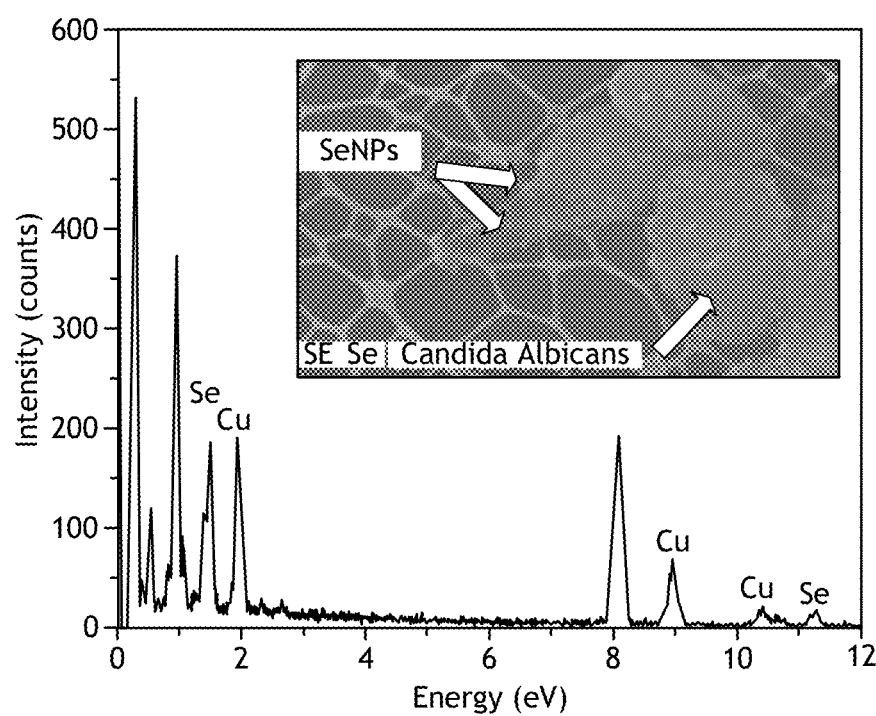
Figure 9A:
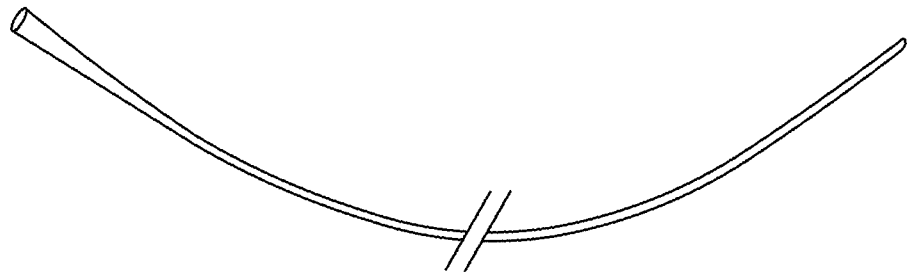
FIG. 9. Example of a medical device, types of Foley catheters. (See world wide web at URL doctorsgates.blogspot.com/2010/05/types-of-foley-catheters.html)
Figure 9B:
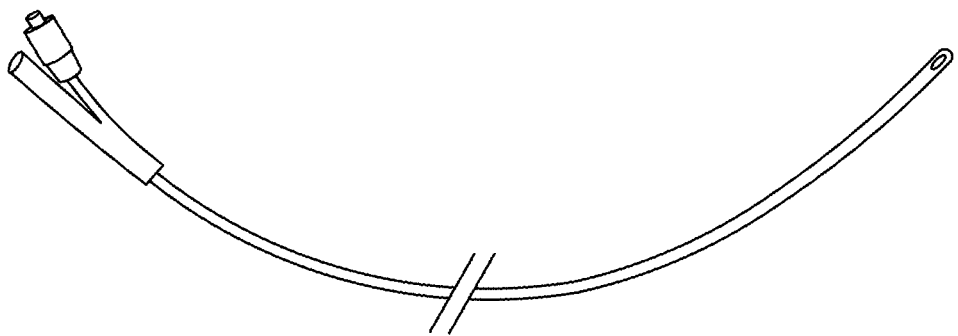
Figure 9C:
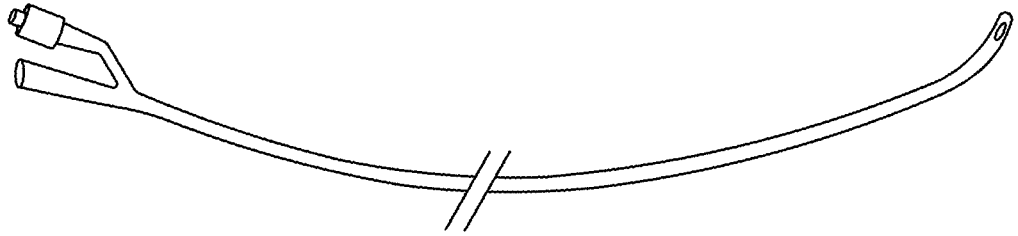
Figure 9D:
Figure 10:
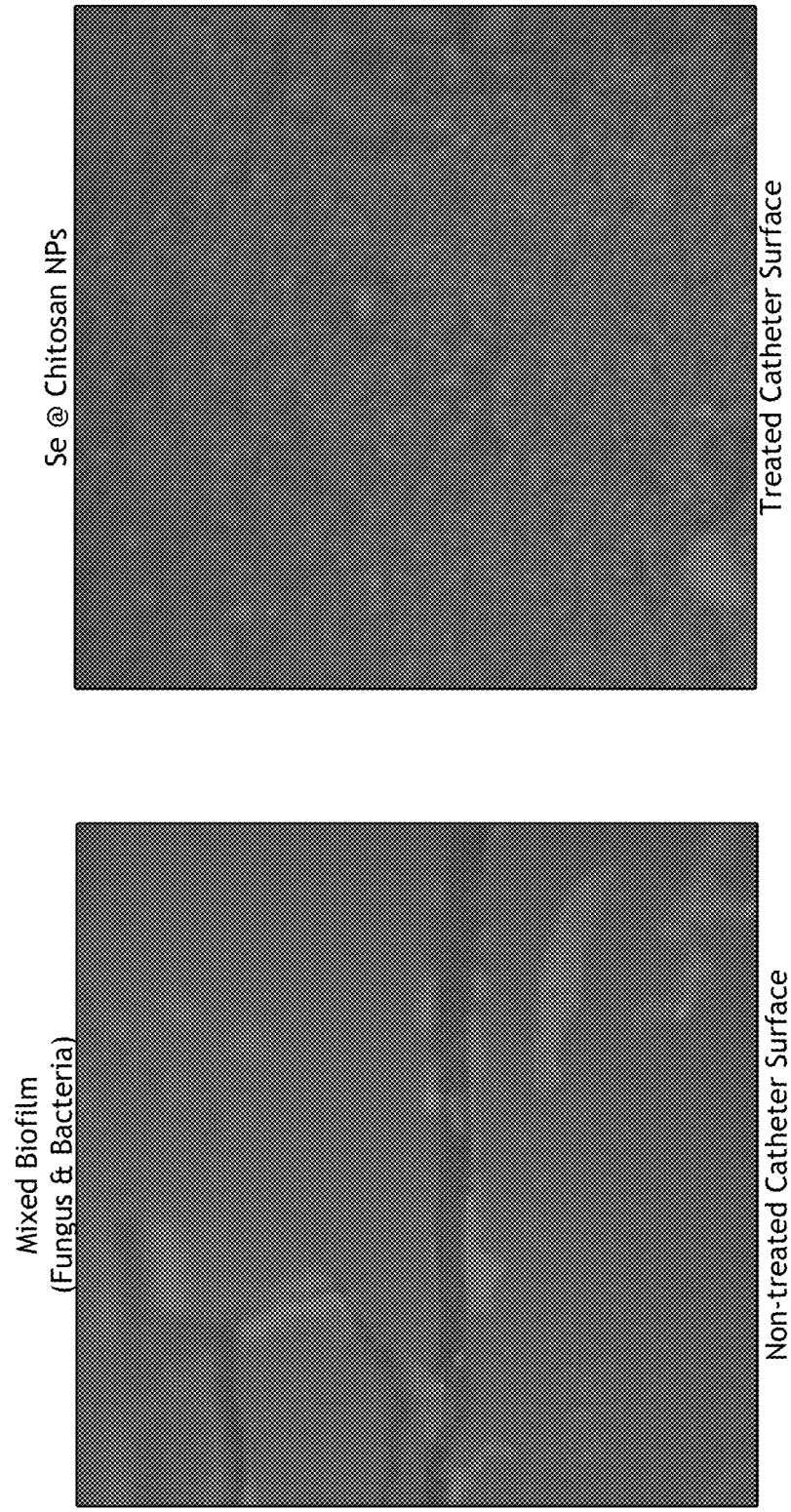
FIG. 10. Comparison of inner catheter wall surface for non-treated (left) and catheter surface treated with 0.0035 mg/mL of CS-SeNPs after 24 hours exposure to mixed biofilm of *C. albicans* and methicillin-resistant *Staphylococcus aureus* (right). On the untreated surface a thick, cracked film is associated with the biofilm.
Figure 11A:
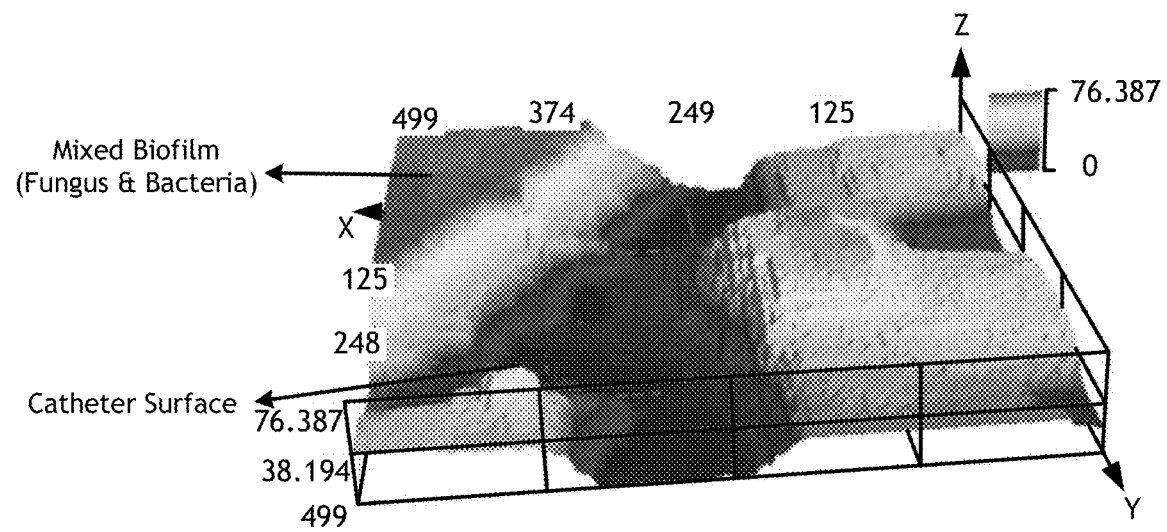
FIG. 11. 3-D Surface analysis of a non-treated inner catheter wall surface having a mixed biofilm on the surface after 24 hours of exposure to microbes. Mixed biofilm growth is observed at thickness between 54 and 77 microns. Dark regions are associated with catheter surface.
Figure 11B:
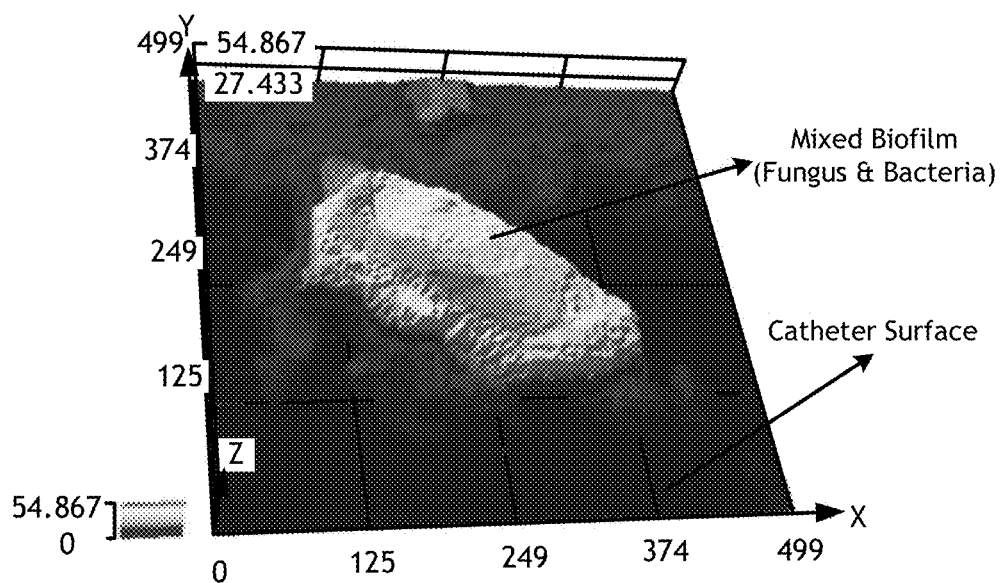
Figure 12:
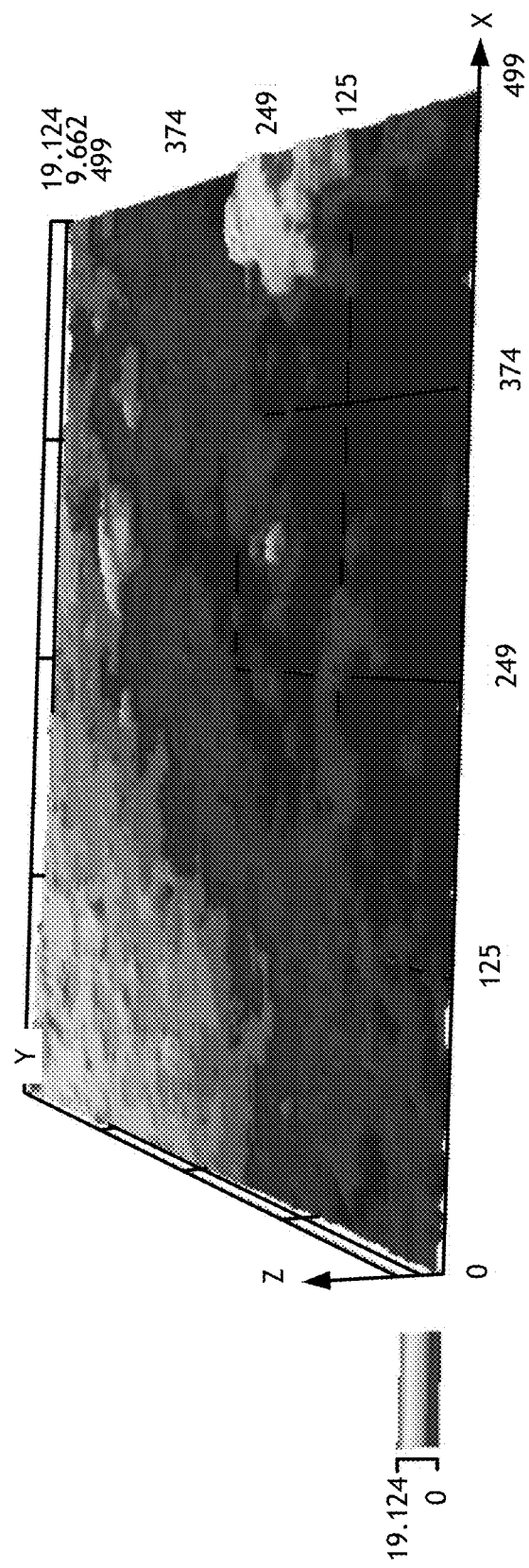
FIG. 12. 3-D Surface analysis (Opto-digital microscope Olympus DSX500) of inner catheter wall surface treated for 24 h with 0.017 mg/mL of CS-SeNPs after 24 hours of exposure to microbes. Minimal growth of mixed biofilm is observed.
Figure 13:
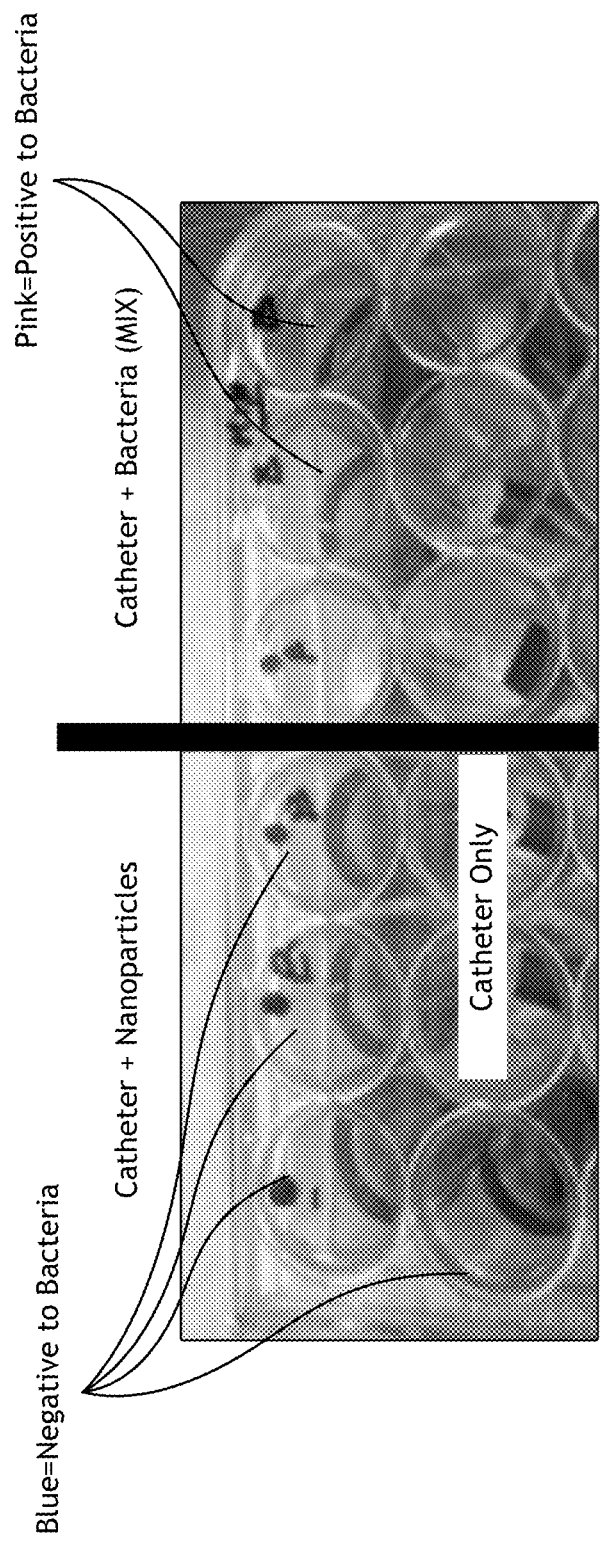
FIG. 13. Enzymatic analysis (PrestoBlue) of non-treated and treated inner catheter wall surface for 24 h with 0.017 mg/mL of CS-SeNPs and after 24 hours of exposure to a mixed biofilm.
Figure 14:
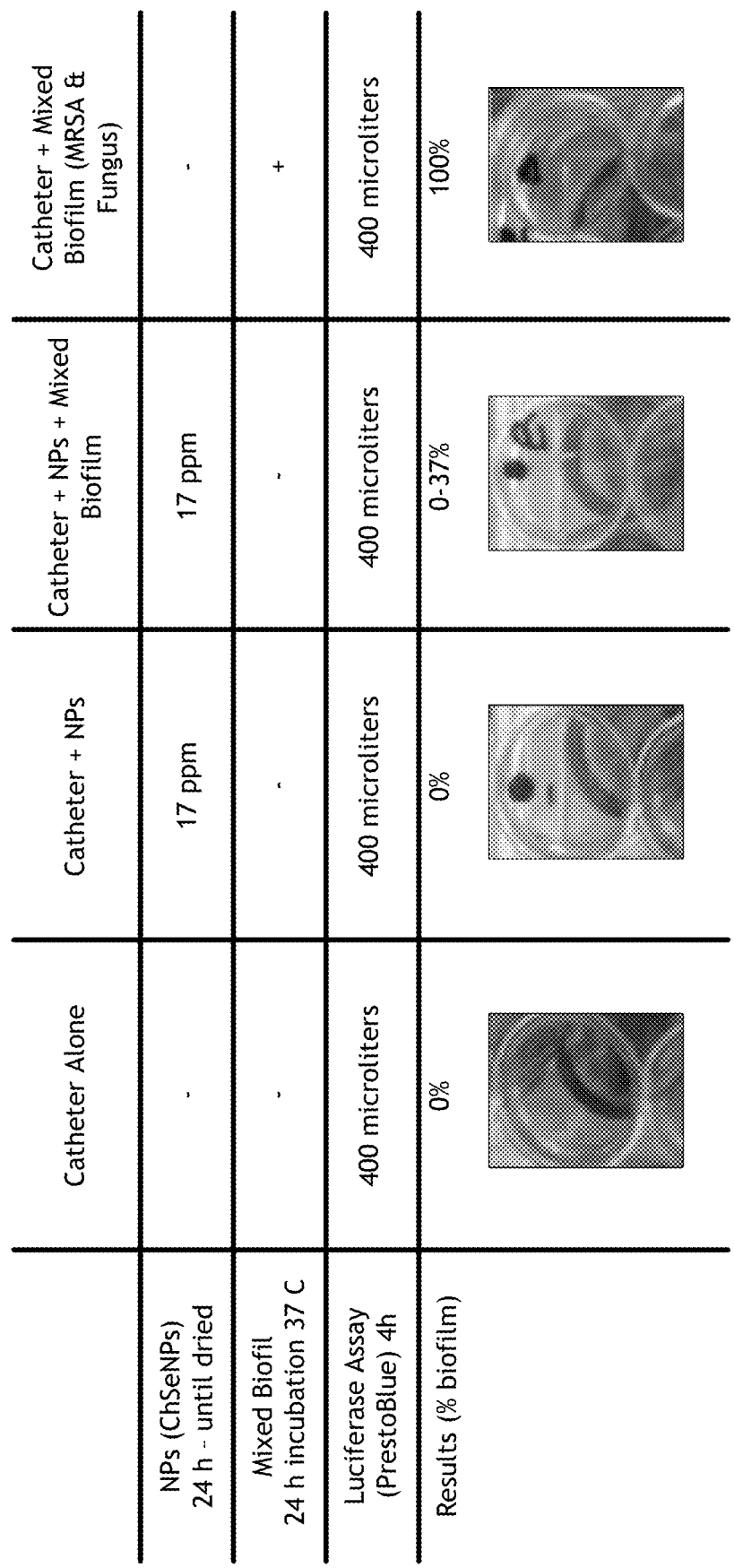
FIG. 14. Summary of enzymatic analysis of non-treated and treated inner catheter wall surface with 0.017 mg/mL of CS-SeNPs after 24 hours of exposure to microbes.
Figure 15:
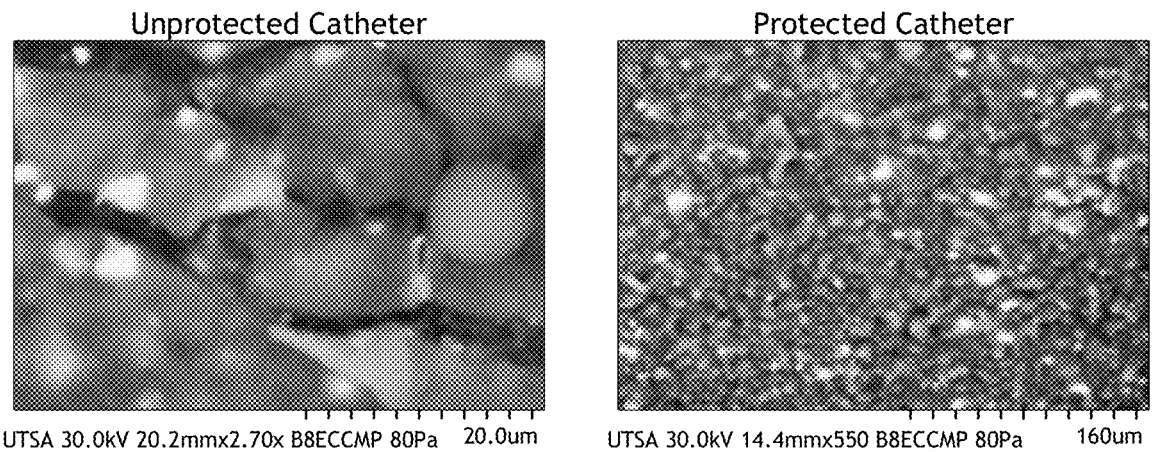
FIG. 15. Scanning electron micrograph (SEM Hitashi 1510) analysis of a non-treated (left) and treated (right) inner catheter wall surface with 0.017 mg/mL of CS-SeNPs after 24 hours of exposure to mixed biofilm.
Figure 15:
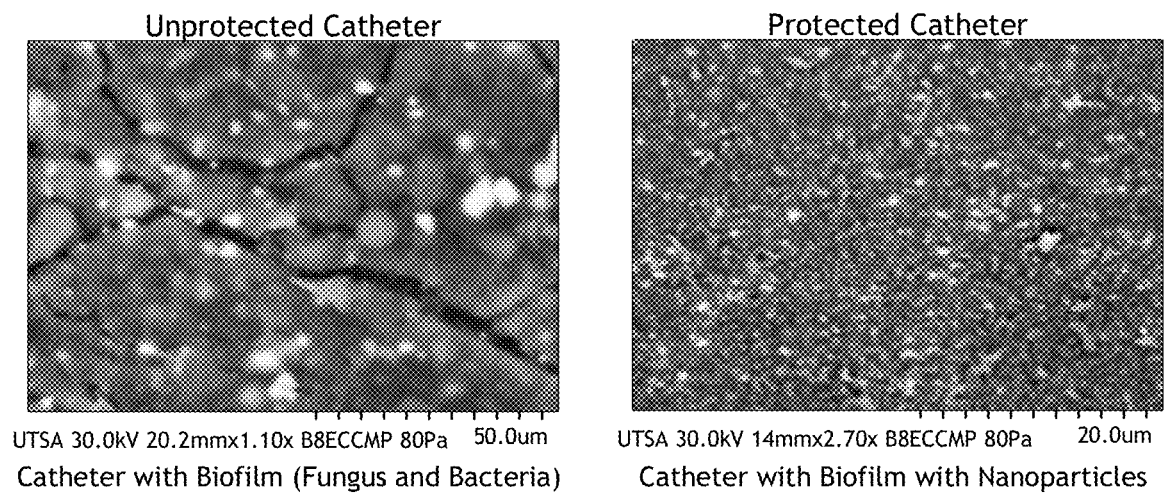

TEM is the most frequently used form of Electron Microscopy (EM). As the primary electrons bypass throughout the tested sample, they produce a two-dimensional (2D) image with excellent structural details. The TEM images showed distortion of the ovoid morphology of the C. albicans after treatment with CS-SeNPs around the outer cell membrane and CS-SeNPs entering inside the cell (FIG. 7). Further, X-ray spectroscopy (EDS) of SeNPs confirmed that selenium metalloid nanoparticles located on the yeast outer cell wall (FIG. 8).

Methodology—

For SEM, briefly, biofilms cultured on 96 well-plates were treated with CS-SeNPs and gently washed twice with PBS before fixing with 4% formaldehyde and 1% glutaraldehyde (GA) for 1 h at room temperature. CS-SeNPs were used at a concentration of 3.5 ppm for inhibition of a pre-formed biofilm. The samples were washed with PBS and then placed in 1% osmium tetroxide (OsO4) solution buffered with PBS for 1 h. The biofilm samples were dehydrated with a series of ethanol solutions (30% for 10 min, 50% for 10 min, 70% for 10 min, 95% for 10 min, and absolute alcohol for 20 min(Fischer et al., Curr. Protoc. Microbiol. 2012, Chapter 2:Unit 2B.2). The specimens were then transferred to 300 mesh carbon-coated copper grids to be observed by SEM in a Hitachi S-5500.

For transmission electron microscopy (TEM), briefly, inoculum from C. albicans cells ($1.5\times10^8$ cells/ml) prepared from 24 h yeast cultures grown at 37° C. in YPD were mixed with CS-SeNPs for 24 h. The treated mature biofilm was then centrifuged at 3500 rpm for 10 min. After washing two times with PBS, cells were fixed in 1 ml of 4% formaldehyde and 1% glutaraldehyde. After 2 h fixation, the samples were stained with 1% OsO4 for 1 h. After washing the Candida cells with PBS to eliminate the heavy metal stain, a dehydration series was performed with 25, 50, 75, 95 and 100% ethanol diluted in $dH_2O$. The absolute dehydration was assured with propylene oxide before embedding in an epoxy resin LX-112 (Ladd Research Industry) and the resin left 48 h at 60° C. to harden. The epoxy resin-embedded sections were cut (90 nm thick) using an ultra-microtome (Leica Microsystems) and a 45 degrees angle diamond knife as previously described (Kuwajima et al., PLoS One 2013, 8:e59573). Ultrathin sections were mounted on an uncoated copper mesh grid and visualized using JEOL JEM-2010F.

Example 6

Synergy

CalcuSyn (Bijnsdorp et al., Methods Mol Biol. 2011, 731:421-34) generated CI values according to the Chou-Talalay method (Chang and Chou, Acta Paediatr Taiwan. 41(6):294-302). The CS-SeNPs combination treatment was synergistic from 160-1.6 to 25000-25 ppm of CS and SeNPs respectively, with CI values <1, for lower doses the effect was antagonistic with CI values CI>1 shown in Table 1. The additive effect of drugs combination depends on the individual dose-effect curves and enables the formulation of synergy, additivity, or antagonism. The dose-effect-based methods depend on the Loewe Additivity model (Foucquier and Guedj, Pharmacol Res Perspect. 2015, 3(3):e00149).

TABLE 1

Data generated by CompuSyn Report.

| Dose (ppm) CS | [A]Biofilm Inhibition (%) | Dose (ppm) SeNPs | [A]Biofilm Inhibition (%) | Dose combination 2500 + 25 ppm CS + SeNPs | [A]Biofilm Inhibition (%) | Fa | [B]CI | |
|---|---|---|---|---|---|---|---|---|
| 2500 | 45 ± 1 | 25 | 59 ± 7 | 2525 | 80 ± 2 | 0.97 | 2.53E−4 | Synergism |
| 1250 | 41 ± 1 | 12.5 | 24 ± 3 | 1262 | 73 ± 3 | 0.908 | 2.91E−4 | (CI < 1) |
| 630 | 26 ± 1 | 6.3 | 23 ± 2 | 636 | 71 ± 1 | 0.887 | 2.45E−4 | |
| 310 | 24 ± 1 | 3.1 | 20 ± 2 | 313 | 46 ± 7 | 0.898 | 9.45E−5 | |
| 160 | 22 ± 1 | 1.6 | 16 ± 4 | 161 | 13 ± 1 | 0.635 | 0.00194 | |
| 80 | 20 ± 2 | 0.8 | 11 ± 5 | 80.8 | 10 ± 1 | 0.095 | 2.32 | Antagonism |

TABLE 1-continued

Data generated by CompuSyn Report.

| Dose (ppm) CS | [A]Biofilm Inhibition (%) | Dose (ppm) SeNPs | [A]Biofilm Inhibition (%) | Dose combination 2500 + 25 ppm CS + SeNPs | [A]Biofilm Inhibition (%) | Fa | [B]CI | |
|---|---|---|---|---|---|---|---|---|
| 40 | 19 ± 1 | 0.4 | 8 ± 4 | 40.4 | 3 ± 1 | 0.063 | 6.25 | (CI > 1) |
| 20 | 7 ± 1 | 0.2 | 3 ± 3 | 20.2 | 1 ± 1 | 0.03 | 65.46 | |
| 10 | 5 ± 1 | 0.1 | 6 ± 3 | 10.1 | 0 ± 0 | 0.01 | 2910 | |
| 5 | 4 ± 1 | 0.05 | 5 ± 5 | 5.05 | 0 ± 0 | 0.006 | 7448 | |
| 2.5 | 3 ± 1 | 0.02 | 1 ± 1 | 2.02 | 0 ± 0 | 0.004 | 24384 | |
| 1.2 | 0 ± 1 | 0.01 | 0 ± 1 | 1.01 | 0 ± 0 | 0.003 | 32414 | |

Example 7

CS-SeNPs in Antimicrobial Coatings on Catheters

Figure 16:
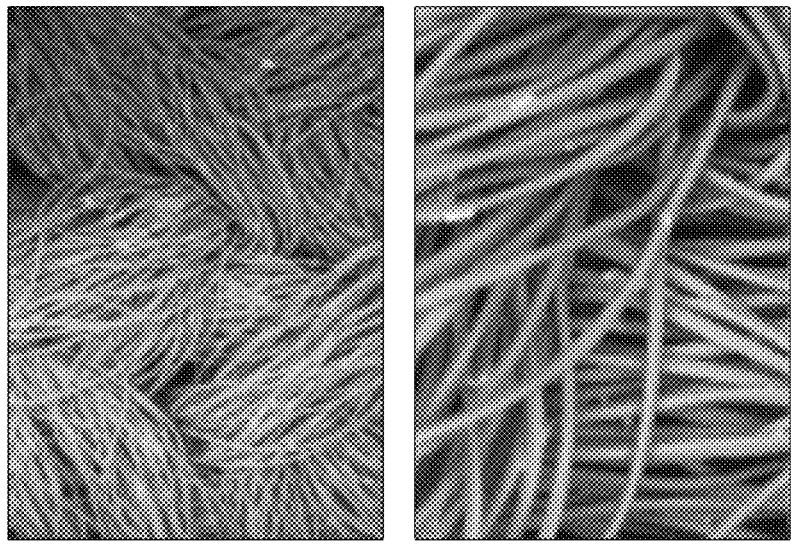
FIG. 16. Scanning electron micrograph analysis of untreated (left) and treated (right) fibers (Bandage elastic wrap) with 0.017 mg/mL of CS-SeNPs after 24 hours of exposure to mixed biofilm. In the untreated sample large pieces of a material associated with mixed (fungal and bacterial) biofilms are observed. The treated sample is shows minimal biofilm growth.
Figure 16:
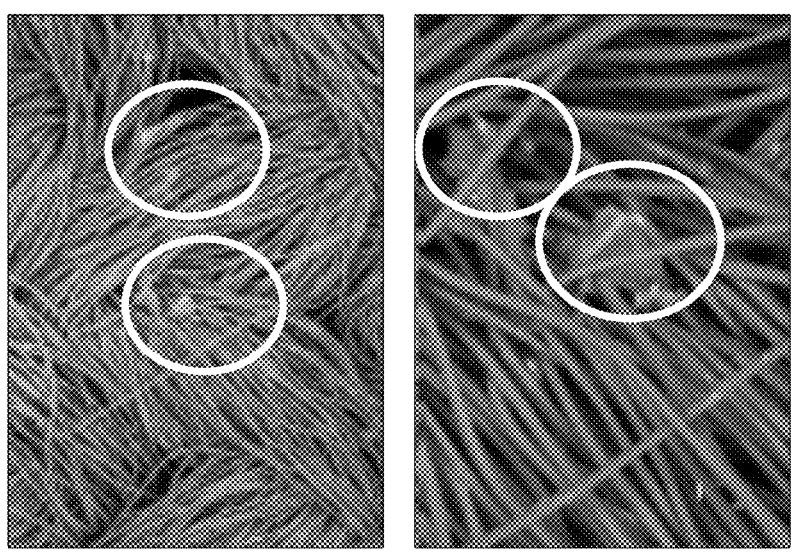
Figure 17A:
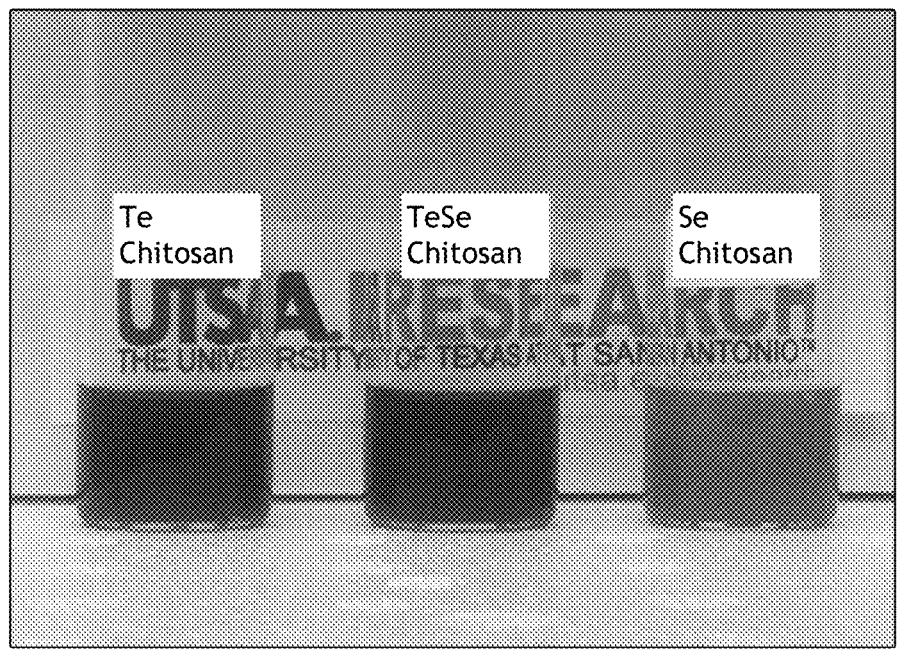
FIG. 17. (a) Photo of the colloidal solutions of Se, Te, and SeTe just after synthesis. (b) Photo of the colloidal solutions of Se, Te, and SeTe just after being washed through acetic acid and Di water (50/50) and re-suspended in a PBS solution.
Figure 17B:
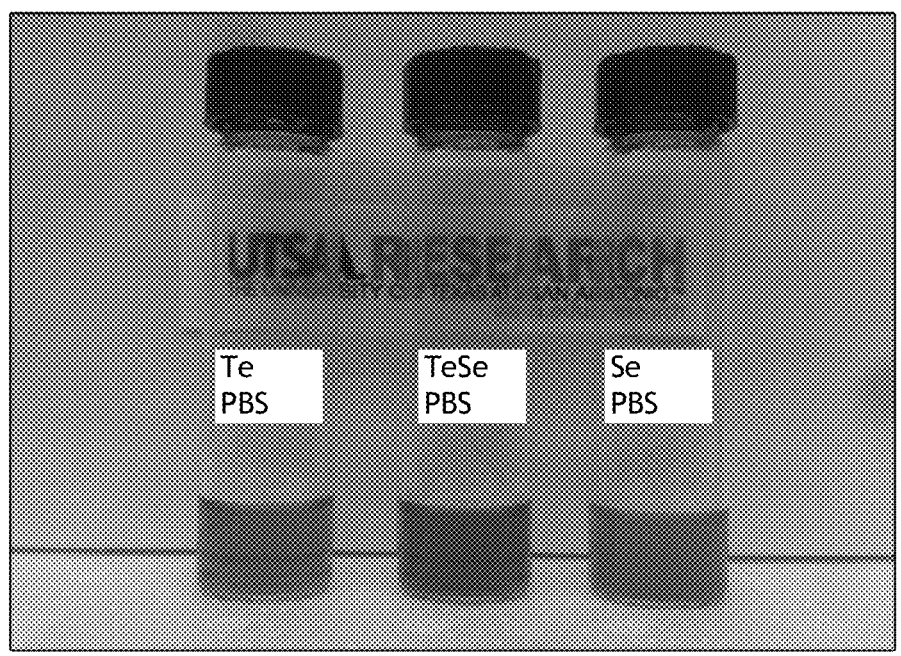
Figure 18A:
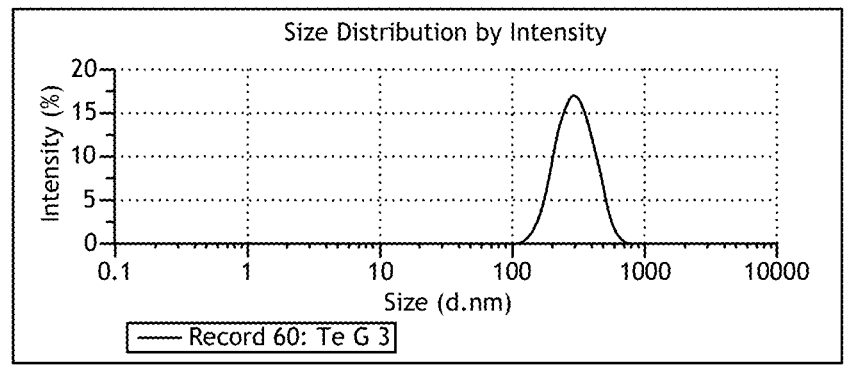
FIG. 18. (a) Histogram of the size distribution of individual CS-TeNPs measured by dynamic light scattering (DLS). The average size of nanoparticles is ~329 nm. (b) The Zeta potential showed a negative charge of 39 mV (after re-suspension in PBS). If the zeta potential is higher than the absolute value ±30 mV then the solution is considered stable while below this value it is unstable and tends to flocculate.
Figure 18B:
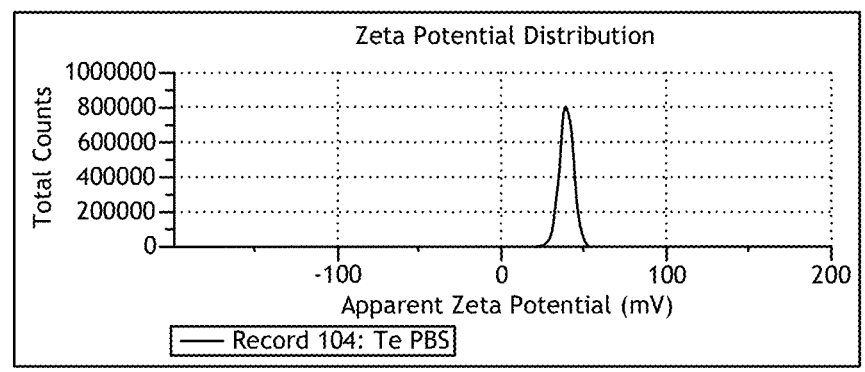
Figure 19A:
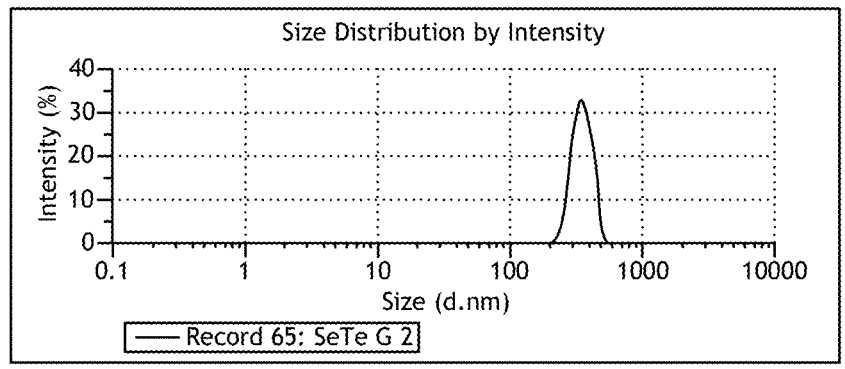
FIG. 19. (a) Histogram of the size distribution of individual CS-SeTeNPs measured by dynamic light scattering (DLS). The average size of nanoparticles is ~360 nm. (b) The Zeta potential showed a positive charge of 63 mV (after re-suspension in PBS). If the zeta potential is higher than the absolute value ±30 mV then the solution is considered stable while below this value it is unstable and tends to flocculate.
Figure 19B:
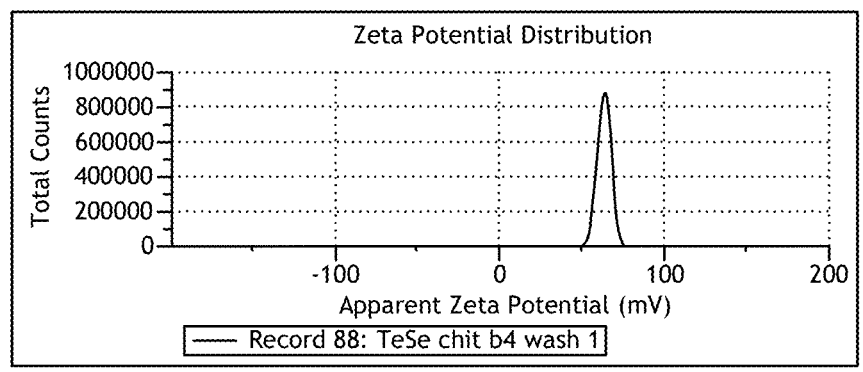

Foley Catheter (indwelling urinary catheter) was coated with CS-SeNPs at 17 ppm on the lumen of the tube for 24 h until dried. A solution containing 50 μL of $1 \times 10^6$ cells/mL of Candida albicans mixed with Methicillin Resistant Staphylococcus aureus (MRSA TCH 1516) at $2 \times 10^7$ cells/ml incubated at 37 C for 24 h on the surface of the lumen of the treated catheter. The resulting biofilm was observed on a Opto-digital microscope Olympus DSX-500 for 3 D images (FIGS. 12-15) to measure the biofilm growth and by electrom microscopy SEM Hitachi 1510 (FIG. 18,19). To quantify the biofilm, we used a viability test Resazurin based using a catheter without coating as positive control, a catheter without coating and biofilm as a negative control (FIGS. 16,17).

Example 8

CS-SeNPs in Antimicrobial Coatings on Textiles

Figure 20:
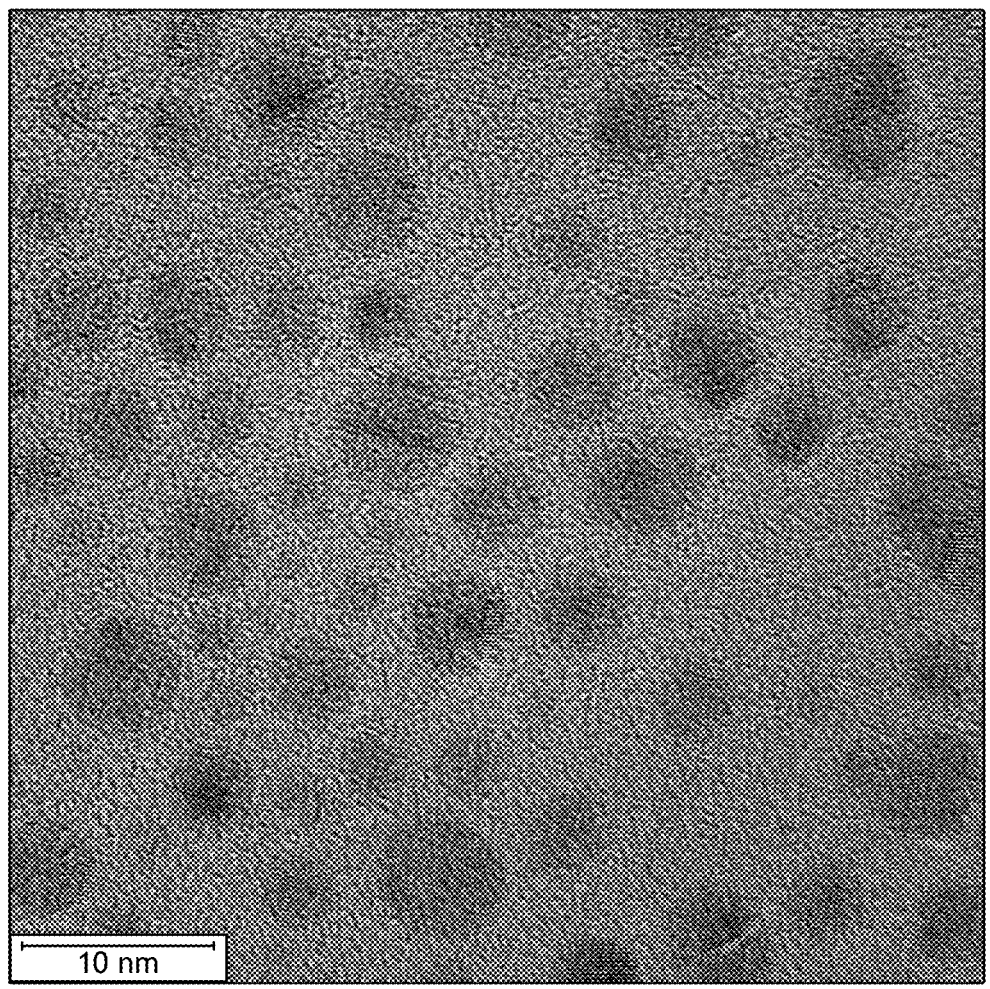
FIG. 20. TEM images of CS-SeNPs.
Figure 21:
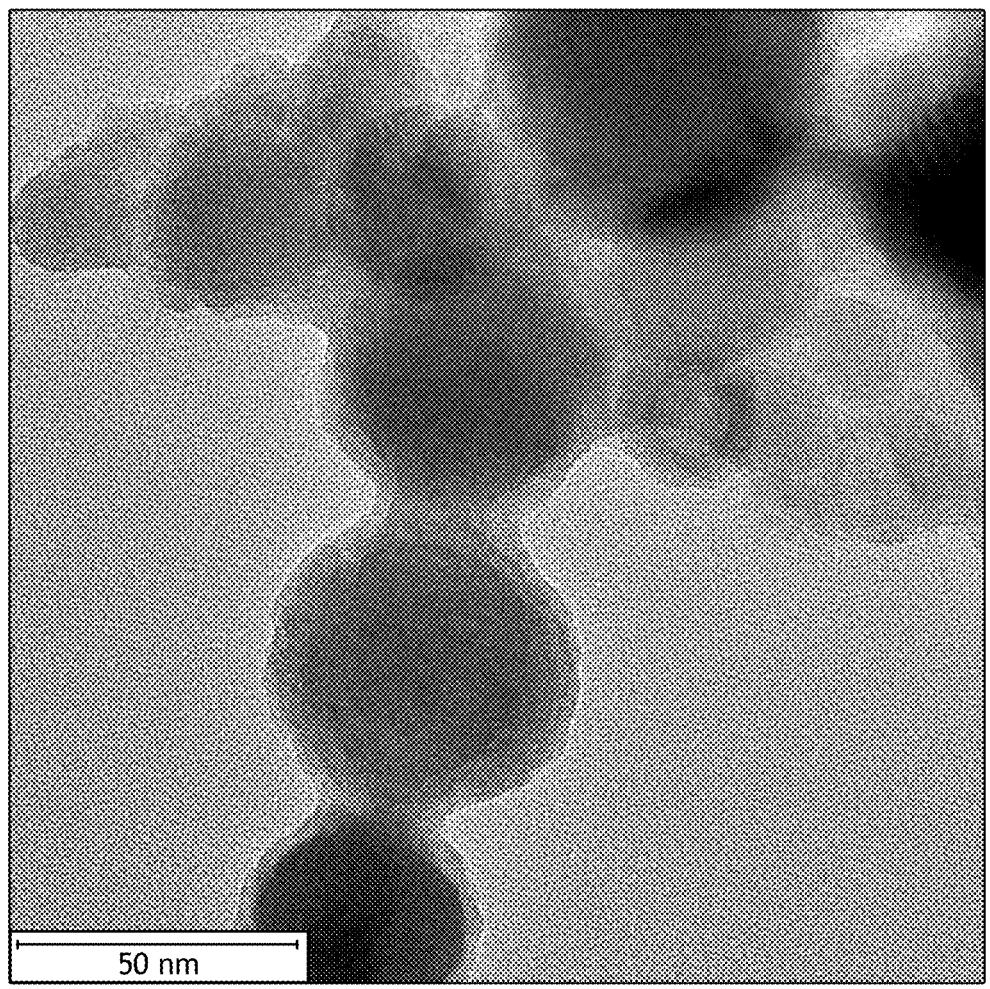
FIG. 21. TEM images of CS-TeNPs.
Figure 22:
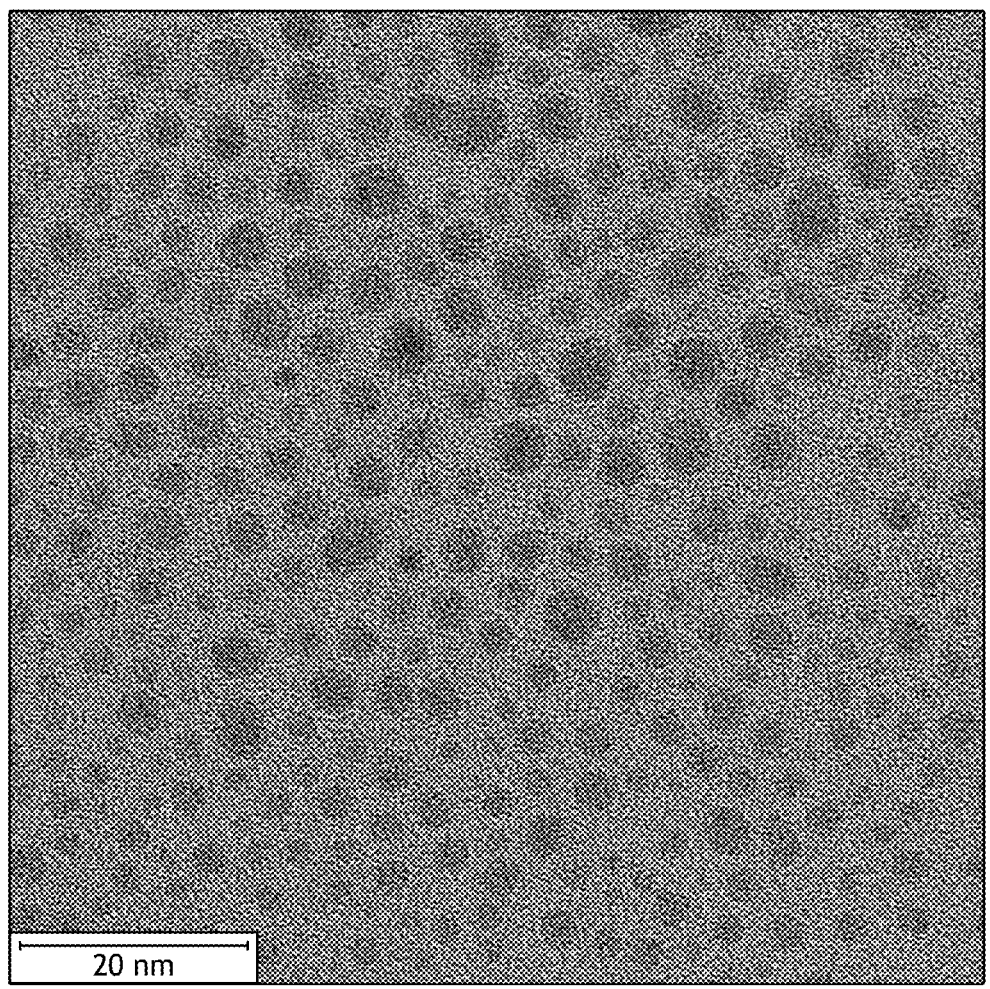
FIG. 22. TEM images of CS-SeTeNPs.

CS-SeNPs (17 ppm) coated or non-coated Bandage elastic wraps (FlexAid) for 24 h. Were tested for anti-microbial properties against mixed multi-resistant bacteria (MRSA) at $2 \times 10^7$ cells/ml incubated at 37 C for 24 h and C. albicans fungus biofilm containing 50 μL of $1 \times 10^6$ cells/mL and incubated at 37 C for 24 h. After incubation with the mixed bacteria the surface of the treated or untreated fibers of the elastic bandage were observed under electron microscopy (SEM Hitashi) 1510 to visualize the presence of mixed biofilms growing on the fibers (FIG. 20). EDX analysis confirmed that the CS-SeNPs adhered to the coated textiles.

Example 9

Synthesis of Tellurium Nanoparticles in the Presence or Absence of Chitosan

Pure tellurium pellets (Sigma-Aldrich) have been placed at the bottom of the glass cuvette and then filled with the liquid (de-ionized water or acetone) having a volume equal to 2 ml. The laser beam is then focused at the surface of the tellurium pellets. The laser used in this experiment is a Nd:YAG laser from EKSPLA NT342B with a pulse duration of 3.6 ns and a repetition rate of 20 Hz, each pulse having a top hat profile. Energy of the laser was monitored during all the duration of the experiment and kept constant at ~20±1 mJ/pulse. Upon focusing this pulse energy corresponds to a fluence of ~2 J cm-2. The irradiation time has been fixed to 15 min. Three different wavelengths have been used i.e. 355 nm (UV), 532 nm (visible) and 1064 nm (NIR). After 15 min irradiation, Te nanoparticles have been produced in DI water with sizes larger than 100 nm while in acetone, much smaller sizes have been attained. (Guisbiers et al. Synthesis of tunable tellurium nanoparticles, Semiconductor Science & Technology, 2017, vol. 32, 04LT01)

Example 10

Synthesis of Chalcogenide Nanoparticles in the Presence or Absence of Chitosan

[00xx] Chitosan solution (0.25 wt. %) is prepared by dissolving an appropriate amount of chitosan in aqueous solution of 0.05 M HCl and its pH is adjusted to ~4.0 using NaOH. The as prepared solution was added to a glass test tube containing 1-2 grams of SeTe, Se or Te pellets with average pellet size of 3-5 mm. The 1064 nm emission line of Nd:YAG pulsed laser is aligned vertically down the center of the test tube and adjusted to focus at the level of the pellets. For all syntheses the pulse repetition rate of the laser is 20 Hz with pulse duration of 3.6 nanoseconds. All samples are irradiated for 15 minutes after which formed nanoparticulates become suspended in the chitosan solution above the solid pellets. The resulting supernatant is extracted from the sample tube, centrifuged at 16,000 rpm and excess chitosan is removed from the pelleted nanoparticles. Following centrifugation, particles are resuspended in 0.05 M solution of acetic acid to further remove access chitosan. The process is repeated and the final suspension of water or phosphate buffer solution is used to resuspend the nanoparticles for characterization or application. The process results in a chitosan coated nanoparticle.

The invention claimed is:

1. A method for producing an antimicrobial coating on a surface, the method comprising: mixing a chitosan capped chalcogenide nanoparticle with an application material to form a mixture; applying the mixture on the surface forming a surface having a chitosan capped chalcogenide nanoparticles on or in the surface that inhibit biofilm formation of bacteria and fungus, wherein the chitosan capped chalcogenide nanoparticle is present in the mixture in an amount from about 0.0001 wt. % to about 10 wt. %.

2. The method of claim 1, wherein the chalcogenide nanoparticle is a selenium nanoparticle.

3. The method of claim 1, wherein the biofilm comprises bacteria, fungi, or combinations thereof.

4. The method of claim 1, wherein the biofilm comprises Streptococcus, Staphylococcus aureus, MRSA, Candida albicans, Pseudomonas aeruginosa, E. coli or combinations of bacterial with fungal biofilms thereof.

5. The method of claim 1, wherein the chitosan capped chalcogenide nanoparticles are present on the surface at a density of 0.01 to 1.0 mg/m$^2$.

6. The method of claim 1, wherein the chitosan capped chalcogenide nanoparticles are present on the surface at a density of about 0.15 mg/m$^2$.

7. The method of claim 1, wherein the chitosan capped chalcogenide nanoparticles have an average diameter greater than or equal to about 20 nanometers and less than or equal to about 100 nanometers.

8. The method of claim 1, wherein the surface is a bandage surface, a catheter surface, a textile surface, a pipe surface, a tube surface, a cooking surface, medical device surface or a bed surface.

* * * * *